United States Patent [19]
Nag

[11] Patent Number: 6,007,820
[45] Date of Patent: Dec. 28, 1999

[54] PURIFICATION AND CHARACTERIZATION OF MHC-PEPTIDE COMPLEXES USEFUL IN AMELIORATING AUTOIMMUNITY

[75] Inventor: Bishwajit Nag, Pacifica, Calif.

[73] Assignee: Anergen, Inc., Redwood City, Calif.

[21] Appl. No.: 08/470,397

[22] Filed: Jun. 6, 1995

Related U.S. Application Data

[60] Division of application No. 08/227,372, Apr. 14, 1994, Pat. No. 5,763,585, which is a continuation-in-part of application No. 08/136,216, Oct. 13, 1993, abandoned.

[51] Int. Cl.$^6$ .................................................. A61K 39/385
[52] U.S. Cl. ..................... 424/193.1; 530/412; 530/413
[58] Field of Search ..................... 530/412, 413; 424/193.1

[56] References Cited

U.S. PATENT DOCUMENTS 5,260,422  11/1993  Clark et al. .

OTHER PUBLICATIONS

Demotz et al. PNAS 88:8730–34, Oct. 1991.

Arnold Bioitechnolgy 9:151–156, Feb. 1991.

*Primary Examiner*—Marianne P. Allen
*Attorney, Agent, or Firm*—Townsend and Townsend and Crew LLP

[57] ABSTRACT

The present invention provides a method for the purification and characterization of MHC-peptide complexes useful in ameliorating immunological disorders, such as, for example, autoimmune diseases, allergic responses and transplant responses. The method disclosed is a one-step method based on the use of metal chelate affinity chromatography to separate the MHC-peptide complexes of interest from both uncomplexed MHC molecules and other endogenous MHC-peptide bound complexes.

14 Claims, 8 Drawing Sheets

```
                    (-)                              His-Gly
N-Ac-Ala-Ser-Ala-Gln-Lys-Arg-Pro-Ser-Gln-Arg-Ser-Lys-Tyr-
                                                     10
      Thr
Leu-Ala-Ser-Ala-Ser-Thr-Met-Asp-His-Ala-Arg-His-Gly-Phe-
                         20
                                                     Ile
Leu-Pro-Arg-His-Arg-Asp-Thr-Gly-Ile-Leu-Asp-Ser-Leu-Gly-
     30                                              40
                    Gly
Arg-Phe-Phe-Gly-Ser-Asp-Arg-Gly-Ala-Pro-Lys-Arg-Gly-Ser-
                         50
              Ser                        Ala
Gly-Lys-Asp-Gly-His-His-Ala-Ala-Arg-Thr-Thr-His-Tyr-Gly-
                    60
                    Ser(-)               Thr
Ser-Leu-Pro-Gln-Lys-Ala-Gln-Gly-His-Arg-Pro-Gln-Asp-Glu-
70                                                   80

Asn-Pro-Val-Val-His-Phe-Phe-Lys-Asn-Ile-Val-Thr-Pro-Arg-
                         90

Thr-Pro-Pro-Pro-Ser-Gln-Gly-Lys-Gly-Arg-Gly-Leu-Ser-Leu-
       100                                           110

Ser-Arg-Phe-Ser-Trp-Gly-Ala-Glu-Gly-Gln-Lys-Pro-Gly-Phe-
                         120

Gly-Thr-Gly-Gly-Arg-Ala-Ser-Asp-Tyr-Lys-Ser-Ala-His-Lys-
                         130

Phe         Val
Gly-Leu-Lys-Gly-His-Asp-Ala-Gln-Gly-Thr-Leu-Ser-Lys-Ile-
140                                                  150

Phe-Lys-Leu-Gly-Gly-Arg-Asp-Ser-Arg-Ser-Gly-Ser-Pro-Met-
                         160

Ala-Arg-Arg-COOH
      170
```

FIG. 1.

| # | HYTYP FREQ.% | DQ | DQB1 | DQA1 | DRB1 | DRB3 | DRB4 | D | DISEASE ASSOCIATION |
|---|---|---|---|---|---|---|---|---|---|
| 1. | 20 | w5(w1) | 1.1 | 1a | 1 | ne | ne | w1 | IDDM(MAJOR), RA(MINOR) |
| 2. | | w5(w1) | 1.1 | 1a | 1 | ne | ne | w20 | |
| 3. | 26 | w6(w1) | 1.2 | 1b | w15(2) | ne | ne | w2 | CPMS, MG(T+) |
| 4. | 1.5 | w6(w1) | 1.12 | 1c | w15(2) | ne | ne | w12 | IDDM(-) |
| 5. | 1.5 | w5(W1) | 1.1 | ? | w16(2) | ne | ne | w12(AZH) | IDDM(+), MG(T-) |
| 6. | ? | w7(w3) | 3.1 | ? | w16(2) | ne | ne | w22 | |
| 7. | 22 | w2 | ? | ? | w17(3) | 24(52) | ne | w3 | IDDM(+), MG(T-) |
| 8. | | w2 | ? | ? | w17(3) | 25(52) | ne | w3 | |
| 9. | ? | w4(Wa) | Wa | ? | w18(3) | ?(52) | ne | ? | |
| 10. | 9 | w8(w3) | 3.2 | 3 | 4 | ne | 53 | w4(4.2) | IDDM(+)(MAJOR), RA(MAJOR), CPMS |
| 11. | 5 | w7(w3) | 3.1 | 3 | 4 | ne | 53 | w4(4.1) | |
| 12. | 3 | w8(w3) | 3.2 | 3 | 4 | ne | 53 | w10 | IDDM(+)(MAJOR), CPMS |
| 13. | 7 | w7(w3) | 3.1 | 3 | 4 | ne | 53 | w13 | |
| 14. | 14 | w8(w3) | 3.2 | 3 | 4 | ne | 53 | w14 | IDDM(+)(MAJOR), RA(MAJOR), CPMS |
| 15. | 0.5 | w4(Wa) | Wa | 7 | 4 | ne | 53 | w15 | |
| 16. | 15 | w7(w3) | 3.1 | 2 | w11(5) | 25(52) | ne | w5 | |
| 17. | | w7(w3) | 3.1 | 2 | w12(5) | 25(52) | ne | B6 | |
| 18. | 10 | w5(w1) | 1.18 | 1c | w(13)(w6) | 24(52) | ne | w18 | |
| 19. | | w5(w1) | 1.18 | 1c | w(13)(w6) | 25(52) | ne | w18 | |
| 20. | 3 | w5(w1) | 1.19 | 1b | w(13)(w6) | 26(52) | ne | w19 | IDDM(MINOR) |
| 21. | 3 | w6(w1) | 1.9 | 1a | w(14)(w6) | 25(52) | ne | w9 | |
| 22. | ? | w6(w1) | 1.16 | 2 | w(14)(w6) | 24(52) | ne | w16 | RA(Minor) |
| 23. | 1 | w9(w3) | 3.3 | 3 | 7 | ne | 53 | w11 | |
| 24. | 27 | w2 | 2 | 3 | 7 | ne | 53 | w17 | |
| 25. | 6 | w4(Wa) | Wa | 1b | ne | w8/52 | ne | w8 | |
| 26. | 2 | ?(w3) | ? | 1b | ne | w8/52 | ne | w8 | |
| 27. | 1 | w9(w3) | 3.3 | 3 | 9 | ne | 53 | w23 | |
| 28. | ? | w5(w1) | 1.1 | 1a | w10 | ? | ? | ? | |

*FIG. 2.*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 170 amino acids
      (B) TYPE: amino acid
      (C) STRANDEDNESS:
      (D) TOPOLOGY: linear (ii) MOLECULE TYPE: protein (iii) HYPOTHETICAL: NO (ix) FEATURE:
      (A) NAME/KEY: Modified-site
      (B) LOCATION: 1
      (D) OTHER INFORMATION: /product= "OTHER"

```
            /note= "Xaa = N-acetyl-alanine"

(ix) FEATURE:
      (A) NAME/KEY: Modified-site
      (B) LOCATION: 3
      (D) OTHER INFORMATION: /product= "OTHER"
            /note= "Xaa = Ala or absent"

(ix) FEATURE:
      (A) NAME/KEY: Modified-site
      (B) LOCATION: 10
      (D) OTHER INFORMATION: /product= "OTHER"
            /note= "Xaa = Arg or His"

(ix) FEATURE:
      (A) NAME/KEY: Modified-site
      (B) LOCATION: 11
      (D) OTHER INFORMATION: /product= "OTHER"
            /note= "Xaa = Ser or Gly"

(ix) FEATURE:
      (A) NAME/KEY: Modified-site
      (B) LOCATION: 16
      (D) OTHER INFORMATION: /product= "OTHER"
            /note= "Xaa = Ser or Thr"

(ix) FEATURE:
      (A) NAME/KEY: Modified-site
      (B) LOCATION: 40
      (D) OTHER INFORMATION: /product= "OTHER"
            /note= "Xaa = Leu or Ile"

(ix) FEATURE:
      (A) NAME/KEY: Modified-site
      (B) LOCATION: 46
      (D) OTHER INFORMATION: /product= "OTHER"
            /note= "Xaa = Ser or Gly"

(ix) FEATURE:
      (A) NAME/KEY: Modified-site
      (B) LOCATION: 59
      (D) OTHER INFORMATION: /product= "OTHER"
            /note= "Xaa = Gly or Ser"

(ix) FEATURE:
      (A) NAME/KEY: Modified-site
      (B) LOCATION: 66
      (D) OTHER INFORMATION: /product= "OTHER"
            /note= "Xaa = Thr or Ala"

(ix) FEATURE:
      (A) NAME/KEY: Modified-site
      (B) LOCATION: 75
      (D) OTHER INFORMATION: /product= "OTHER"
            /note= "Xaa = Ala or Ser"

(ix) FEATURE:
      (A) NAME/KEY: Modified-site
      (B) LOCATION: 76
      (D) OTHER INFORMATION: /product= "OTHER"
            /note= "Xaa = Gln or absent"

(ix) FEATURE:
      (A) NAME/KEY: Modified-site
      (B) LOCATION: 80
      (D) OTHER INFORMATION: /product= "OTHER"
            /note= "Xaa = Pro or Thr"

(ix) FEATURE:
      (A) NAME/KEY: Modified-site
      (B) LOCATION: 141
      (D) OTHER INFORMATION: /product= "OTHER"
            /note= "Xaa = Leu or Phe"

(ix) FEATURE:
      (A) NAME/KEY: Modified-site
      (B) LOCATION: 144
      (D) OTHER INFORMATION: /product= "OTHER"
            /note= "Xaa = His or Val"
```

```
    (ix) FEATURE:
          (A) NAME/KEY: Protein
          (B) LOCATION: 1..170
          (D) OTHER INFORMATION: /note= "Myelin basic protein"

(xi) SEQUENCE DESCRIPTION: SEQ ID NO:1:

Xaa Ser Xaa Gln Lys Arg Pro Ser Gln Xaa Xaa Lys Tyr Leu Ala Xaa
1               5                   10                  15

Ala Ser Thr Met Asp His Ala Arg His Gly Phe Leu Pro Arg His Arg
            20                  25                  30

Asp Thr Gly Ile Leu Asp Ser Xaa Gly Arg Phe Phe Gly Xaa Asp Arg
        35                  40                  45

Gly Ala Pro Lys Arg Gly Ser Gly Lys Asp Xaa His His Ala Ala Arg
    50                  55                  60

Thr Xaa His Tyr Gly Ser Leu Pro Gln Lys Xaa Xaa Gly His Arg Xaa
65              70                  75                  80

Gln Asp Glu Asn Pro Val Val His Phe Phe Lys Asn Ile Val Thr Pro
            85                  90                  95

Arg Thr Pro Pro Ser Gln Gly Lys Gly Arg Gly Leu Ser Leu Ser
            100                 105                 110

Arg Phe Ser Trp Gly Ala Glu Gly Gln Lys Pro Gly Phe Gly Tyr Gly
            115                 120                 125

Gly Arg Ala Ser Asp Tyr Lys Ser Ala His Lys Gly Xaa Lys Gly Xaa
    130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170

(2) INFORMATION FOR SEQ ID NO:2:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

His His His His His His Tyr Asp Pro Val Val His Phe Phe Lys Asn
1               5                   10                  15

Ile Val Thr Pro Arg Thr Pro Pro Ser
            20                  25

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Tyr Asp Pro Val Val His Phe Phe Lys Asn Ile Val Thr Pro Arg Thr
1               5                   10                  15

Pro Pro Pro Ser
            20

(2) INFORMATION FOR SEQ ID NO:4:
```

```
      (i) SEQUENCE CHARACTERISTICS:
          (A) LENGTH: 20 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:4:

Gly Phe Gly Tyr Gly Gly Arg Ala Ser Asp Tyr Lys Ser Ala His Lys
1               5                   10                  15

Gly Phe Lys Gly
            20
```

PURIFICATION AND CHARACTERIZATION OF MHC-PEPTIDE COMPLEXES USEFUL IN AMELIORATING AUTOIMMUNITY

This application is a division of U.S. application Ser. No. 08/227,372, filed Apr. 14, 1994, now U.S. Pat. No. 5,763,585 which is a continuation-in-part of U.S. application Ser. No. 08/136,216, filed Oct. 13, 1993, now abandoned all of which are hereby incorporated in their entirety by reference.

FIELD OF THE INVENTION

The present invention relates to compositions useful for the modulation of T cell function in the treatment of immunological disorders such as, for example, autoimmune diseases, allergic responses and transplant rejections. In particular, it relates to a method for preparing a composition comprising a plurality of MHC-peptide complexes having a defined composition. These complexes, which target T helper ($T_H$) cells, consist essentially of an isolated major histocompatibility complex (MHC) component and a peptide representing a fragment of an antigen associated with the disease state to be treated. These MHC-peptide complexes can be further conjugated with radioisotopes or other labels for diagnostic purposes, or to toxins and other substances which render the complexes therapeutically useful.

BACKGROUND OF THE INVENTION

Unwanted T cell activation is known to be associated with a number of pathological, immunological disorders such as, for example, autoimmune diseases, allergic responses and transplant rejections. Autoimmune diseases are a particularly important class of the diseases involving deleterious or unwanted immune responses. In autoimmune diseases, self-tolerance is lost and thus, the immune system attacks "self" tissue as if it were a foreign target. More than 30 autoimmune diseases are presently known to exist; myasthenia gravis (MG) and multiple sclerosis (MS), for example, are two autoimmune diseases which have received wide-spread public attention.

Moreover, a number of allergic diseases have been found to be associated with particular MHC alleles or have been suspected of having an autoimmune component. Additionally, other deleterious T cell-mediated responses include the destruction of foreign cells that are purposely introduced into the body as grafts or transplants from allogeneic hosts. This process, known as "allograft rejection," involves the interaction of host T cells with foreign MHC molecules. Quite frequently, a broad range of MHC alleles are involved in the response of the host T cell to an allograft.

The current model of immunity postulates that antigens mobilize an immune response, at least in part, by being ingested by an antigen-presenting cell (APC) which contains on its surface a MHC Class II glycoprotein encoded by a gene in the major histocompatibility complex (MHC). The antigen is then presented to a specific T helper cell in the context of the surface bound MHC glycoprotein. By interaction of the antigen specific T cell receptor with the antigen-MHC complex, the T helper cell is stimulated to mediate the antigen-specific immune response, including the induction of cytotoxic T cell function, the induction of B cell function, and the secretion of a number of factors aiding and abetting this response.

The involvement of the MHC Class II proteins in autoimmune diseases has been shown in animal models. Administration of antibodies either to the MHC Class II proteins themselves or to the agents that induce expression of the MHC Class II genes interferes with the development of the autoimmune condition in these model systems. The role of T helper cells has also been demonstrated in these models by counteracting the autoimmune system using anti-CD4 monoclonal antibodies; CD4 is the characteristic T helper cell receptor (Shizuru, et al., *Science* 240:659–662 (1988)).

Recent experiments have shown that, under certain circumstances, anergy or nonresponsiveness can be induced in autoreactive lymphocytes (See, e.g., Schwartz, *Cell* 1073–1081 (1989), which is incorporated herein by reference). In vitro experiments suggest that antigen presentation by MHC Class II molecules in the absence of a co-stimulatory signal induces a state of proliferative non-responsiveness in syngeneic T cells (Quill, et al., *J. Immunol.* 138:3704–3712 (1987), which is incorporated herein by reference). These reports, however, provide no clear evidence that induction of anergy in vivo is possible or that autoimmune disease can be effectively treated in this manner.

More recently, complexes and methods have been described that are useful for identifying and inhibiting those aspects of the immune system that are responsible for undesirable immune responses, such as, for example, autoimmunity. See, U.S. Pat. Nos. 5,130,297 and 5,194,425, both of which are incorporated herein by reference. These complexes and methods are designed to target T helper cells which recognize a particular antigen in association with a glycoprotein encoded by the MHC. The complexes effectively bind T cell receptors and cause non-responsiveness in target T-lymphocytes and other cells of the immune system.

These complexes, which are useful for modulating T cell function, consist of (1) an effective portion of the MHC-encoded antigen-presenting glycoprotein; and (2) a peptide representing a fragment of an autoantigen or other antigenic sequence associated with the disease state to be treated (i.e., an antigenic peptide). The association between the antigenic peptide and the MHC glycoprotein can be by covalent or noncovalent bonding. Evidence from both in vitro and in vivo experiments unequivocally establishes that such complexes induce clonal anergy in syngeneic T cells.

The MHC component of these complexes is typically prepared by purification from cell surfaces. However, purified MHC molecules isolated from cell surfaces usually contain prebound endogenous peptides. (See, Chicz, et al., *Nature* 358:764–768 (1992) which is incorporated herein by reference.) When using MHC-peptide complexes to modulate T-cell function, it is desirable to use a composition of homogeneous complexes of an MHC molecule and a defined antigenic peptide entity. A major limitation in obtaining such a composition lies in the inability of the previously used purification method to successfully separate the MHC-peptide complexes of interest from both uncomplexed MHC molecules and other endogenous MHC-peptide complexes.

To date, the only method used to separate the MHC class II-peptide complexes of interest from free MHC molecules or endogenous peptide bound-MHC complexes involves the use of a biotin-avidin system. (See, Demotz, et al., *Proc. Nat'l Acad. Sci. U.S.A.* 88:8730–8734, which is incorporated herein by reference.) This method has limitations in the sense that it involves modification of the peptide component in order to prevent side reactions during biotinylation. Moreover, using this method, recovery of the purified product can vary significantly, and the purified complexes have been found to have some residual contaminations. To overcome this latter problem, another anti-hapten antibody affinity chromatography was added prior to the avidin column chromatography. This additional step, involving the addition of a DNP ligand to the peptide, reduces the recovery of the purified complexes even further to only about 0.4 to 4 percent of the starting complexes.

Thus, there still remains a need for purification methods that are easy to carry out, readily scalable and wherein the recovery of the purified MHC-peptide complexes is relatively high.

SUMMARY OF THE INVENTION

The present invention provides a method for the purification and characterization of MHC-peptide complexes useful in ameliorating immunological disorders, such as, for example, autoimmune diseases, allergic responses and transplant responses. These complexes consist essentially of (1) an effective portion of the MHC-encoded antigen-presenting glycoprotein; and (2) a peptide representing a fragment of an autoantigen or other antigenic sequence associated with the disease state to be treated (i.e., an antigenic peptide). The method disclosed for the purification of such complexes is a one-step method based on the use of metal chelate affinity chromatography to separate the MHC-peptide complexes of interest from both uncomplexed MHC molecules and other endogenous MHC-peptide bound complexes.

Generally, the purification method comprises: a) isolating an MHC component from a cell which produces the component, the MHC component having an antigen binding site or sites; b) incorporating at least one metal-chelating amino acid into an antigenic peptide; c) contacting the MHC component with the antigenic peptide such that the peptide is associated with the antigen binding site of the MHC component, thereby forming a MHC-peptide complex; d) contacting the MHC-peptide complex with a solid support having attached thereto a metal ion specific for the metal-chelating amino acid of the peptide, whereby the MHC-peptide complex is bound to the metal ion of the solid support; and e) eluting the bound MHC-peptide complex from the solid support. This purification method is easy to use, readily scalable and the recovery of the purified MHC-peptide complexes of interest is high.

Additionally, the present invention provides a composition comprising a plurality of MHC-peptide complexes of defined composition. These compositions are designed to target T helper cells which recognize a particular antigen in association with a glycoprotein encoded by the MHC. The complexes bind T cell receptors and cause non-responsiveness in target T-lymphocytes and other cells of the immune system.

Other advantages, objects, features and embodiments of the present invention will become apparent from the detailed description which follows.

BRIEF DESCRIPTION OF THE DRAWINGS

FIG. 1 shows the amino acid sequence of myelin basic protein. (SEQ ID NO:1.)

FIG. 2 presents a list of the DQ/DR haplotypes in humans and their associations with autoimmune diseases.

DETAILED DESCRIPTION OF THE INVENTION AND PREFERRED EMBODIMENTS

Figure 3:
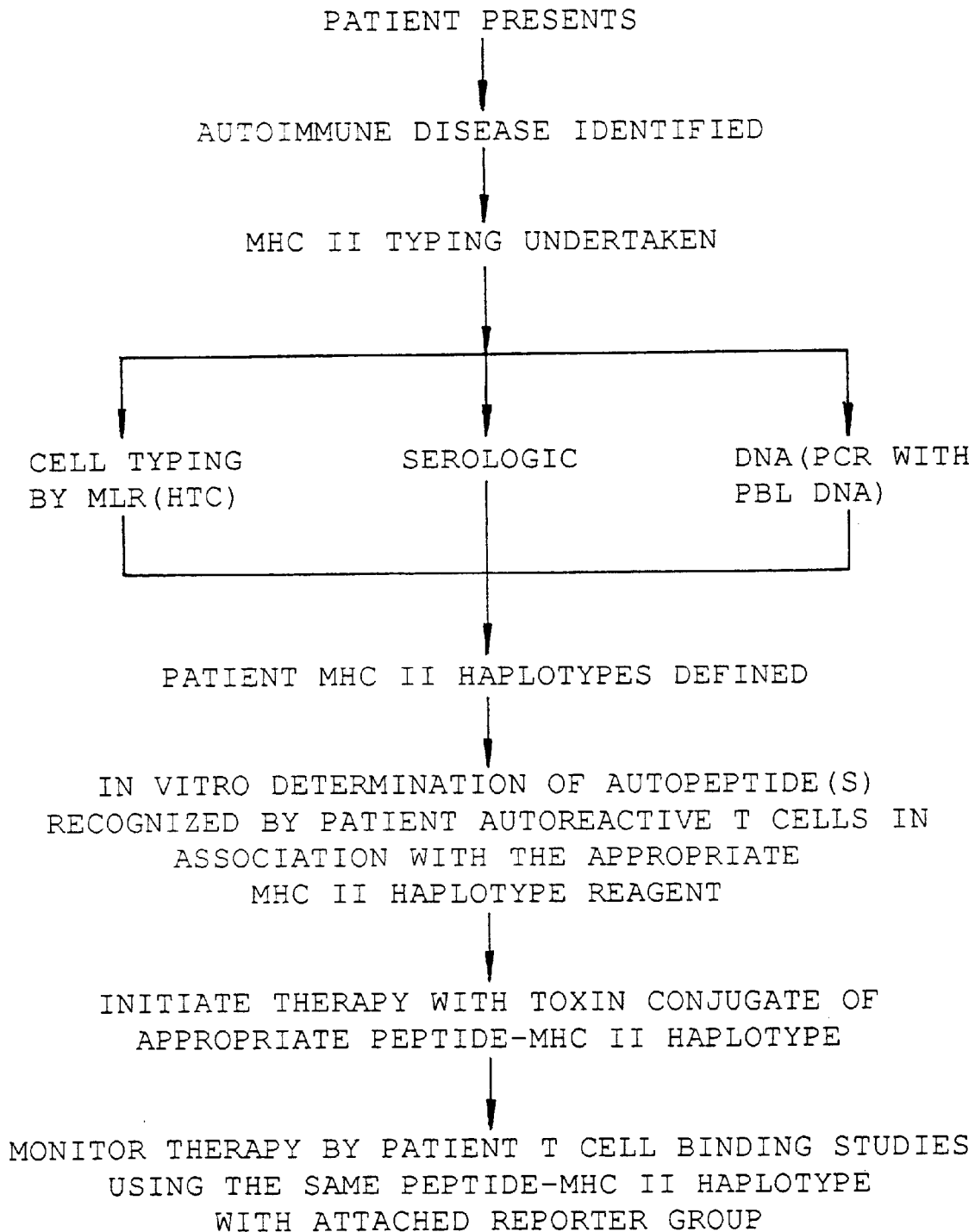
FIG. 3 shows a protocol suitable for the utilization of the complexes of the invention for the diagnosis and/or treatment of an autoimmune disease.

The present invention provides a method for preparing a composition comprising a plurality of MHC-peptide complexes of defined composition, the method comprising: a) isolating an MHC component from a cell which produces the component, the MHC component having an antigen binding site; b) contacting the MHC component with an antigenic peptide such that the peptide is associated with the antigen binding site of the MHC component, thereby forming an MHC-peptide complex, the antigenic peptide having incorporated therein at least one metal-chelating amino acid; c) contacting the MHC-peptide complex with a solid support having attached thereto a metal ion specific for the metal-chelating amino acid of the peptide, whereby the MHC-peptide complex is bound to the metal ion of the solid support; and d) eluting the bound MHC-peptide complex from the solid support.

Once formed, this composition of homogenous MHC-peptide complexes can be used to modulate T cell function in the treatment of immunological disorders such as, for example, autoimmune diseases, allergic responses and transplant rejections. In addition, the purified complexes of the present invention can be used as vaccines to promote immune responses. When used in this embodiment, the MHC component (either Class I or Class II) is typically modified to allow attachment to a competent antigen presenting cell bearing ligands involved in the co-stimulatory signal. Alternatively, the complex may be linked to isolated co-stimulatory ligands such that T cell proliferation is induced. Thus, T cells will respond to the antigenic peptide presented by the complexes and an immune response will be initiated.

The complexes of the present invention contain at least two components: (1) a peptide representing a fragment of an autoantigen or other antigenic sequence associated with the disease state to be treated (i.e., an antigenic peptide); and (2) an effective portion of an MHC-encoded glycoprotein involved in antigen presentation. An effective portion of an MHC glycoprotein is one which comprises an antigen binding site and the sequences necessary for recognition of the MHC-peptide complex by the appropriate T cell receptor. The MHC component can be either a Class I or a Class II molecule. The association between the peptide antigen and the antigen binding site of the MHC protein can be by covalent or noncovalent bonding. Additionally, the MHC-peptide complex may contain an effector component which is generally a toxin or a label. The effector portion may be conjugated to either the MHC-encoded glycoprotein or to the autoantigenic peptide. Complexes containing an effector component are disclosed and claimed in U.S. Pat. No. 5,194,425, supra.

Each aspect of the presently disclosed method for the purification and characterization of MHC-peptide complexes useful in ameliorating immunological disorders (such as, for example, autoimmune diseases, allergic responses and transplant rejections) will be described in great detail below.

Isolation Of The MHC-Derived Component

As previously stated, the present invention provides a method for preparing a composition comprising a plurality of MHC-peptide complexes of defined composition. As used herein, the term "of defined composition" refers to a plurality of MHC-peptide complexes wherein at least 50 percent, usually above 60 percent, preferably about 75 percent, and more preferably about 95 percent of the complexes are identical and free from uncomplexed MHC molecules or other endogenous MHC-peptide complexes. An endogenous MHC-peptide complex is one comprising a peptide which is associated with the MHC molecule when the molecule is isolated from a cell that expresses the MHC molecule. In the initial step of this method, an MHC component, having an antigen binding site or sites, is isolated from a cell which produces such components. The MHC component can be readily isolated using the methods and procedures set forth herein.

The glycoproteins encoded by the major histocompatibility complex have been extensively studied in both the human and murine systems. In general, they have been classified as Class I glycoproteins, which are found on the surfaces of all cells and primarily recognized by cytotoxic T cells; and Class II glycoproteins, which are found on the surface of several cells, including accessory cells such as macrophages, and which are involved in the presentation of antigens to T helper cells. Some of the histocompatibility proteins have been isolated and characterized. For a general review of MHC glycoprotein structure and function, see, e.g., *Fundamental Immunology* (2d Ed., W. E. Paul, (ed.), Ravens Press, N.Y. (1989)), which is incorporated herein by reference. The term "isolated MHC component" as used herein refers to an MHC glycoprotein or an effective portion of an MHC glycoprotein (i.e., one comprising an antigen binding site or sites and the sequences necessary for recognition by the appropriate T cell receptor) which is in other than its native state (i.e., not associated with the cell membrane of the cell that normally expresses MHC). As described in detail below, the MHC component is preferably solubilized from an appropriate cell source. For human MHC molecules, human lymphoblastoid cells are particularly preferred as sources for the MHC component.

The MHC glycoprotein portions of the complexes of the invention, then, can be obtained by isolation from lymphocytes and screened for their ability to bind the desired peptide antigen. The lymphocytes are from the species of individual which will be treated with the complexes once formed. They may be isolated, for example, from the human B cells of an individual suffering from the targeted autoimmune disease, which have been immortalized by transformation with a replication deficient Epstein-Barr virus, utilizing techniques known to those in the art.

MHC glycoproteins have been isolated from a multiplicity of cells using a variety of techniques including, for example, solubilization by treatment with papain, by treatment with 3M KCl and by treatment with detergent. In a preferred method, detergent extraction of Class II protein from lymphocytes followed by affinity purification is used. The detergent can subsequently be removed by dialysis or through the use of selective binding beads, e.g., Bio Beads.

Methods for purifying the murine I-A (Class II) histocompatibility proteins have been disclosed by Turkewitz, et al., *Molecular Immunology* (1983) 20:1139–1147, which is incorporated herein by reference. These methods, which are also suitable for Class I molecules, involve the preparation of a soluble membrane extract from cells containing the desired MHC molecule using nonionic detergents, such as, for example, NP-40, TWEEN™80 and the like. The MHC molecules are then purified by affinity chromatography, using a column containing antibodies raised against the desired MHC molecule. Use of 0.02% TWEEN™-80 in the elution buffer is helpful for eliminating aggregation of the purified molecules.

The isolated antigens encoded by the I-A and I-E subregions have been shown to consist of two noncovalently bonded peptide chains: an alpha chain of 32–38 kD and a beta chain of 26–29 kD. A third, invariant, 31 kD peptide is noncovalently associated with these two peptides, but it is not polymorphic and does not appear to be a component of the antigens on the cell surface (Sekaly, *J. Exp. Med.* (1986) 164:1490–1504, which is incorporated herein by reference). The alpha and beta chains of seven allelic variants of the I-A region have been cloned and sequenced.

The human Class I histocompatibility proteins have also been studied. The MHC of humans (HLA) on chromosome 6 has three loci, HLA-A, HLA-B, and HLA-C, the first two of which have a large number of alleles encoding alloantigens. These are found to consist of a 44 kD subunit and a 12 kD $beta_2$-microglobulin subunit which is common to all antigenic specificities. Isolation of these detergent-soluble HLA antigens was described by Springer, et al., *Proc. Natl. Acad. Sci. USA* (1976) 73:2481–2485; Clementson, et al., in "Membrane Proteins" (Azzi, A., ed.); Bjorkman, P., Ph.D. Thesis Harvard (1984), all of which are incorporated herein by reference.

Alternatively, since the amino acid sequences of a number of MHC glycoproteins are known and the genes have been cloned, one may express the desired MHC glycoprotein in a recombinantly engineered cell such as, for example, bacteria, yeast, insect (especially employing baculoviral vectors), and mammalian cells using conventional techniques know to those of skill in the art. It is expected that those of skill in the art are knowledgeable in the numerous expression systems available for expression of the DNA encoding the MHC glycoproteins. As such, no attempt will be made to describe in detail the various methods known for the expression of proteins in prokaryotes or eukaryotes.

In brief, the expression of natural or synthetic nucleic acids encoding MHC polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the perilipin proteins. To obtain high level expression of a cloned gene, it is desirable to construct expression plasmids which contain, at the minimum, a strong promoter to direct transcription, a ribosome binding site for translational initiation, and a transcription/translation terminator.

Prokaryotic expression systems suitable for expressing the MHC glycoproteins include, but are not limited to, the following: *E. coli, Bacillus sp.* and Salmonella (Palva, et al., Gene 22:229–235 (1983); Mosbach, et al., *Nature* 302:543–545 (1983), with *E. coli* expression systems being presently preferred. Moreover, eucaryotic expression systems suitable for expressing the MHC glycoproteins include, for example, mammalian, yeast or insect cells.

The transformed cells are then cultured under conditions favoring expression of the MHC sequence and the recombinantly produced protein recovered from the culture. The recombinant MHC protein can be purified using conventional techniques known to those of skill in the art. In particular, it will be understood by those of skill that a metal binding domain, e.g., a sequence encoding a polyhistidine sequence, can be incorporated into the nucleic acid encoding the MHC polypeptides prior to their expression using standard techniques. Subsequently, the recombinantly produced MHC polypeptides containing the metal binding domain can be purified using metal chelate chromatography. (See, section pertaining to "Metal Chelate Affinity Chromatography," infra.)

For a general overview of the techniques employed in the recombinant expression of MHC glycoproteins, see, for example, Sambrook, et al., *Molecular Cloning: A Laboratory Manual* (2nd Ed., Vols. 1–3, Cold Spring Harbor Laboratory (1989)), *Methods in Enzymology,* Vol. 152: *Guide to Molecular Cloning Techniques* (Berger and Kimmel (eds.), San Diego: Academic Press, Inc. (1987)), or *Current Protocols in Molecular Biology,* (Ausubel, et al. (eds.), Greene Publishing and Wiley-Interscience, New York (1987), all of which are incorporated herein by reference.

The Antigenic Peptide

In order to separate the MHC-peptide complexes of interest from both uncomplexed MHC molecules and other endogenous MHC-peptide complexes, at least one metal-chelating amino acid is incorporated into the autoantigenic or antigenic peptide of interest. As used herein, the term "metal-chelating amino acid" is used to refer to an amino acid that is capable of participating in metal binding, i.e., an amino acid that is capable of forming a chelate or complex with a metal ion. Metal-chelating amino acids include, but are not limited to, the following: glycine, tyrosine, cysteine, histidine, arginine, lysine, asparagine and methionine. In a presently preferred embodiment, histidine is the metal-chelating amino acid incorporated into the antigenic peptide. Moreover, as will be explained below, in one embodiment, from two to about ten metal-chelating amino acids (e.g., histidines) are incorporated into the antigenic peptide.

Antigenic proteins or tissues for a number of autoimmune diseases are known. In experimentally induced autoimmune diseases, for example, the following antigens involved in pathogenesis have been characterized: native type-II collagen has been identified in collagen-induced arthritis in rat and mouse, and mycobacterial heat shock protein in adjuvant arthritis (Stuart, et al., (1984), *Ann. Rev. Immunol.* 2:199–218; van Eden, et al., (1988), *Nature* 331:171–173.); thyroglobulin has been identified in experimental allergic thyroiditis (EAT) in mouse (Maron, et al., (1988), *J. Exp. Med.* 152:1115–1120); acetyl choline receptor (AChR) has been identified in experimental allergic myasthenia gravis (EAMG) (Lindstrom, et al. (1988), *Adv. Immunol.* 42:233–284); and myelin basic protein (MBP) and proteolipid protein (PLP) have been identified in experimental allergic encephalomyelitis (EAE) in mouse and rat (See Acha-Orbea, et al., supra). In addition, target antigens have been identified in humans: type-II collagen has been identified in human rheumatoid arthritis (Holoshitz, et al., (1986), *Lancet* ii:305–309); and acetyl choline receptor in myasthenia gravis (Lindstrom, et al., (1988), supra). All of the above references are incorporated herein by reference.

It is believed that the presentation of antigen by the MHC glycoprotein on the surface of antigen-presenting cells (APCs) occurs subsequent to the hydrolysis of the antigenic proteins into smaller peptide units. The location of these smaller segments within the antigenic protein can be determined empirically. These segments are thought to be about 8 to about 18 residues in length and to contain both the agretope (recognized by the MHC molecule) and the epitope (recognized by the T cell receptor on the T-helper cell). The epitope itself is a contiguous or non-contiguous sequence of about 5 to about 6 amino acids which recognizes the antigen-specific receptor of T-helper cells. The agretope is a continuous or non-contiguous sequence which is responsible for the association of the peptide with the MHC glycoproteins.

The empirical process of determining the relevant 8-18 amino acid subunits is illustrated below using the alpha subunit of the acetylcholine receptor (AChR) of skeletal muscle which is known to be involved in myasthenia gravis. It is will be apparent to those skilled in the art that, using the process set forth below, one can readily determine the relevant 8-18 amino acid subunit for antigens associated with other immune disorders.

In myasthenia gravis (MG), autoantibodies against the alpha subunit of the acetylcholine receptor (AChR) are associated with the autoimmune response directed at the AChR. Eighty five percent of MG patients have autoantibodies reactive with the alpha subunit. Of these, 60% have antibodies that bind to a peptide segment of the alpha subunit called the main immunogenic region (MIR) which is located between residues 60 and 80 (Tzartos and Lindstrom, *Proc. Natl. Acad. Sci. USA* (1980) 77:755). The peptide segments recognized by autoreactive human T cells are also located on the alpha subunit (Hohfield, et al., *Proc. Natl. Acad. Sci. USA* (1987). The epitopes recognized by these T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQw2 MHC haplotypes, respectively (See, Acha-Orbea (1989), supra).

The peptides carrying agretopes permitting presentation of the epitopes associated with the alpha subunit of this receptor are readily determined. For example, determination of the appropriate peptides in a mouse model is carried out as follows.

Strains of mice, which when immunized with Torpedo californicus AChR develop a disease with many of the features of human myasthenia gravis, are used as the model. MHC Class II glycoproteins are isolated from spleen cells of these mice using lectin and monoclonal antibody affinity supports. The purified MHC Class II proteins are incorporated into phospholipid vesicles by detergent dialysis. The resultant vesicles are then allowed to fuse to clean glass cover slips to produce on each cover slip a planar lipid bilayer containing MHC molecules (See, Brian and McConnell, *Proc. Natl. Acad. Sci. USA* (1984) 81:6159, which is incorporated herein by reference).

One cover slip containing MHC Class II molecules embedded in the adherent planar lipid membrane is placed in each well of several 24-well culture plates. Each one of the approximately 40 overlapping 20-residue synthetic peptides corresponding to the alpha subunit sequence and containing one or more radiolabeled amino acid residues (prepared as described below) is placed in a well with cover slip and PBS, and allowed to incubate several days. The extent of binding of peptide in the MHC Class II glycoprotein antigen binding site is measured by the amount of radioactivity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this manner, the set of agretopes for the alpha subunit of AChR is defined for the mouse strain that displays the symptoms of MG upon immunization with AChR or purified alpha subunit.

Next, each of the alpha subunit synthetic peptide segments that contain an agretope is again incorporated into the antigen binding site of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well. T cell hybridoma proliferation, as measured by tritiated thymidine uptake into DNA, indicates that the MHC Class II protein-bound peptide contains both an agretope and an epitope for binding to the T cell. Activation of T cell clones is determined by measuring IL-3 production (See, Quill, et al., supra).

The Dupont apparatus and technique for rapid multiple peptide synthesis (RAMPS) are used to synthesize the members of a set of overlapping (10 residue overlap), 20-residue peptides from the alpha subunit of Torpedo californicus AChR. The sequence of this peptide is known. One or more radioactive amino acids is incorporated into each synthetic peptide- The pentafluorophenyl active esters of side chain-protected, FMOC amino acids are used to synthesize the peptides, applying standard stepwise solid phase peptide synthetic methods, followed by standard side chain deprotection and simultaneous release of the peptide amide from the solid support.

Alternatively, the overlapping sequences which include the putative segments of 8-18 amino acids of the antigenic protein, such as acetylcholine receptor protein, can be synthesized using the method of Geysen, et al., *J. Immun. Meth.* (1987) 102:274, which is incorporated herein by reference. The synthesized radiolabeled peptides are subsequently tested by incubating them individually (on the plates) with purified MHC proteins which have been formulated into lipid membrane bilayers as described above.

As previously explained, using the above disclosed procedure, one of skill in the art can readily determine the relevant 8-18 amino acid subunit for the antigens associated with other immune disorders. In multiple sclerosis (MS), which results in the destruction of the myelin sheath in the central nervous system, it is known that myelin basic protein (MBP) (i.e., the major protein component of myelin) is the principal autoantigen. Pertinent segments of the MBP protein can also be determined empirically using the procedure described above and a strain of mice which develops experimental allergic encephalitis (EAG) when immunized with bovine myelin basic protein. The sequence of MBP (Sequence I.D. No. 1) is shown in FIG. 1.

Moreover, although systemic lupus erythematosus (SLE) has a complex systemology, it is known to result from an autoimmune response to red blood cells. Peptides which are the antigenic effectors of this disease are found in the proteins on the surface of red blood cells. Rheumatoid arthritis (RA), a chronic inflammatory disease, results from an immune response to proteins found in the synovial fluid. Insulin-dependent diabetes mellitus (IDDM) results from autoimmune attack on the beta cells within the Islets of Langerhans which are responsible for the secretion of insulin. Circulating antibodies to Islets cells surface antigens and to insulin are known to precede IDDM. Critical peptides in eliciting the immune response in IDDM are believed to be portions of the insulin sequence and the beta cell membrane surface proteins.

Thus, in summary, a set of labeled test peptides is prepared and those which bind to an MHC in planar lipid membranes containing MHC proteins are shown to contain the agretope. The identified peptides are then prepared by conventional solid phase synthesis, and the subset which contains epitopes for the disease-inducing T-helper cell clones is determined by incubation of the candidate peptides with murine antigen-presenting cells (APC) (or with isolated MHC complex) and spleen or lymph node T cells from mice immunized with the full length protein. Successful candidates will stimulate T cell proliferation in this system. This second, smaller subset represents the suitable peptide component.

Once determined, the relevant antigenic peptide subunits can be readily synthesized using standard automated methods for peptide synthesis being that they are relatively short in length. Alternatively, they can be made recombinantly using isolated or synthetic DNA sequences, but this is not the most efficient approach for peptides of this length. Moreover, in order to be able to separate the MHC-peptide complexes of interest from both uncomplexed MHC molecules and other endogenous MHC-peptide bound complexes, at least one metal-chelating amino acid is incorporated into the autoantigenic or antigenic peptide of interest. The metal-chelating amino acid(s) can be readily incorporated into the relevant antigenic peptide during peptide synthesis.

As previously explained, a metal-chelating amino acid is one which is capable of participating in metal binding, i.e., an amino acid that is capable of forming a chelate or complex with a metal ion. Such amino acids include: glycine, tyrosine, cysteine, histidine, arginine, lysine, asparagine and methionine. In a presently preferred embodiment, histidine is the metal-chelating amino acid incorporated into the antigenic peptide. Again, since the relevant antigenic sequences are relatively short in length, they can be readily synthesized using standard automated methods for peptide synthesis. In doing so, at least one metal-chelating amino acid is incorporated at either the N- or the C-terminus of the protein. Preferably, from two to about ten metal-chelating amino acids are incorporated into the antigenic peptide. More preferably, about six metal-chelating amino acids are incorporated into the antigenic peptide. Alternatively, the antigenic peptide tagged with at least one metal-chelating amino acid can be made recombinantly using isolated or synthetic DNA sequences. This, however, is not the most efficient approach for peptides of this length.

The Effector Component

Additionally, the complexes of the invention can be designed to destroy the immune response to the peptide in question. In this instance, the MHC-peptide complex will contain an effector component. The effector portion of the MHC-peptide molecule can be, for example, a toxin, a chemotherapeutic agent, an antibody to a cytotoxic T-cell surface molecule, a lipase, or a radioisotope emitting "hard" radiation (e.g., beta radiation). A number of protein toxins are well known in the art and include, for example, ricin, diphtheria, gelonin, Pseudomonas toxin, and abrin. Chemotherapeutic agents include, but are not limited to, doxorubicin, daunorubicin, methotrexate, cytotoxin, and anti-sense RNA. Moreover, antibiotics can also be used as the effector component. Antibodies have been isolated to cytotoxic T-cell surface molecules and these may thus operate as toxins. In addition, radioisotopes such as yttrium-90, phosphorus-32, lead-212, iodine-131, or palladium-109 can be used. The emitted radiation effects the destruction of the target T-cells.

In some cases the active portion of the effector component is entrapped in a delivery system such as a liposome or dextran carrier; in these cases, either the active component or the carrier may be bound in the complex.

If the effector molecule is intended to be a label, a gamma-emitting radioisotope such as technetium-99 or indium-111 can be used. In addition, other types of labeling such as fluorescence labeling by, for example, fluorescein can be used.

The effector component can be attached to the MHC glycoprotein or, if its nature is suitable, to the peptide portion. Iodine 131 or other radioactive labels, for example, can often be included in the peptide determinant sequence.

Complexes containing an effector component are disclosed and claimed in U.S. Pat. No. 5,194,425, supra.

Formation of the MHC-Peptide Complex

Once the MHC component has been isolated and the antigenic peptide tagged with at least one metal-chelating amino acid has been synthesized, these two elements can be associated with one another to form an MHC-peptide complex using standard means known in the art. The antigenic peptides can be associated noncovalently with the pocket portion of the MHC protein by, for example, mixing the two components together. Excess peptide can be removed using a number of standard procedures, such as, for example, by ultrafiltration or by dialysis.

Metal Chelate Affinity Chromatography

Once the MHC-peptide complexes have been formed, they are ready to be purified. The purification method of the present invention is based on the use of metal chelate affinity chromatography to separate the MHC-peptide complexes of interest from both uncomplexed MHC molecules and other endogenous MHC-peptide bound complexes. Since its introduction in 1975 by Porath, et al. (*Nature* 258:598–599 (1975)), metal chelate affinity chromatography has been used to purify proteins. See, e.g., Lonnerdal and Keen, *J. Appl. Biochem.* 4:203–208 (1982); Sulkowski, *Trends in Biotechnology* 3:1–7 (1985).

Generally, metal chelate affinity chromatography takes advantage of the reversible interaction between metal ions (such as, for example, $Cu^{2+}$, $Zn^{2+}$, $Ni^{2+}$, etc.) and electron donor groups situated on the surface of proteins, especially the imidazole side-chain of histidine. By immobilizing metal ions on a chromatography solid support or matrix through the use of a chelating ligand (i.e., by forming a chelate resin), a protein having an accessible electron donor group can be separated from protons lacking such groups. The protein binds to the immobilized metal ions when the pH is such that the electron donor group is at least partially unprotonized. The bound protein can subsequently be eluted using a number of different techniques such as, for example, by competitive elution, by lowering the pH or, by using strong chelating agents.

Metal ions suitable for use in accordance with the present purification method include, but are not limited to, the first-row transitions metals. The first-row transition metals include, for example, $Cu^{2+}$, $Zn^{2+}$, $Ni^{2+}$, $Co^{2+}$ and $Fe^{3+}$. In a presently preferred embodiment, $Ni^{2+}$, $Cu^{2+}$ and $Zn^{2+}$ are the metal ions used. It has been found that these metals readily form a complex or chelate with metal-chelating amino acids and thus, they can be used to separate those proteins having a metal-chelating amino acid(s) from those which do not.

Metal-chelating amino acids suitable for use in accordance with the present method include those that are capable of participating in metal binding, i.e., those amino acids that are capable of forming a chelate or complex with a metal ion. Metal-chelating amino acids include, but are not limited to, the following: glycine, tyrosine, cysteine, histidine, arginine, lysine, asparagine and methionine. In a presently preferred embodiment, histidine is the metal-chelating amino acid incorporated into the antigenic peptide. Since histidine is a relatively rare amino acid, accounting for only about 2% of the amino acids in most globular proteins (Klapper, M. H., *Biochem. Biophys. Res. Commun.* 78:1018 (1977)), selective separation of histidine-tagged polypeptides from a complex mixture can be achieved under both native and denatured conditions. Moreover, in a presently preferred embodiment, from two to about ten metal-chelating amino acids are incorporated into the antigenic peptide using standard automated methods for peptide synthesis. In a more preferred embodiment, about six metal-chelating amino acids are incorporated into the antigenic peptide.

A chelating ligand is used to link the metal ion to the solid support or chelating matrix. The particular chelating ligand employed is not a critical aspect of the present invention. Any chelating ligand can be used provided that the ligand strongly complexes the metal ions while permitting reversible interactions between the metal ions and the protein to be purified. Chelating ligands suitable for use in accordance with the present method include, but are not limited to, the following: iminodiacetic acid ("IDA"), N,N,N'-tris (carboxymethyl)ethylenediamine ("TED"), N-carboxymethyl aspartate, N,N,N,N,N-carboxymethyl tetraethylenepentamine and nitrilotriacetic acid ("NTA"). Certain of these chelating ligands are presently preferred, namely, IDA, TED and NTA. When $Ni^{2+}$ is the metal ion used, NTA, i.e., nitrilotriacetic acid, is the presently preferred chelating ligand. When charged with $Ni^{2+}$, nitrilotriacetic acid is especially useful for the purification of proteins containing neighboring histidine residues. The use of nitrilotriacetic acid as a chelating ligand is described in U.S. Pat. No. 5,047,513, which is incorporated herein by reference.

The chelating ligand is covalently bound to a solid support or, alternatively, a chelating matrix using conventional methods and techniques known to and understood by those skilled in the art. The solid support, having the chelating ligand bound thereto, is subsequently charged with a metal ion. As with the chelating ligand, the solid support employed is not a critical aspect of the present invention. Materials suitable for use as the solid support include those materials commonly used in affinity and gel chromatography. Examples of such materials include, but are not limited to, the following: dextran, agarose, cellulose, polystyrene, polyacrylamide, and their derivatives. In a presently preferred embodiment, agarose or a derivative thereof (such as, for example, Sepharose™ (Pharmacia Biosystems, Uppsala, Sweden)) is used as the solid support.

The solid support, charged with the metal ion, can be used batch-wise or in a chromatography column. In a presently preferred embodiment, the solid support is packed into a column (e.g., 14.5 cm×1.6 cm), and equilibrated with an aqueous buffer that does not form chelates with the metal ion employed. It will be readily apparent to those skilled in the art that the dimensions of the column can be varied depending upon the quantity of protein to be purified. Moreover, it will be readily apparent to those of skill in the art that a number of different aqueous buffers can be used provided they do not form chelates with the metal ion employed. Equilibration buffers suitable for use in the present method include, for example, a sodium or potassium phosphate buffer (pH 7-8) or a Tris-HCl buffer (pH 7.0).

Once formed, the MHC-peptide complexes (in equilibrating buffer) are contacted with the solid support in either a batch or column format. The MHC-peptide complexes containing a metal-chelating amino acid in the peptide component of the complexes will chelate with the metal ion and thus, be bound to the solid support. The solid support is then washed with equilibrating buffer to remove the uncomplexed MHC molecules and other MHC-peptide complexes, neither of which will bind to the solid support due to the absence of a metal-chelating amino acid. Additionally, the solid support can be washed with a number of different reagents to remove residual contaminations due to disulfide cross links, hydrophobic interactions, low affinity binding to the resin, etc. As such, the equilibrating buffer can contain a denaturing agent or a detergent, such as, for example, guanidine, NaCl, ethanol, glycerol, urea, Tween™ or Triton™.

Finally, the bound MHC-peptide complexes of interest are eluted from the column by washing the solid support with an elution buffer. The elution buffer can be of a constant pH or can be applied as a pH gradient. The elution buffer can contain either a Lewis acid, i.e., an electron acceptor, which competes with the metal for the protein, or a Lewis base, i.e., an electron donor, which competes with the protein for the metal. In a presently preferred embodiment, the elution buffer used is 0.05M imidazole; imidazole will compete with the protein for the metal coordination sites thereby displacing the MHC-peptide. The optimal elution conditions are dependent on the amount and type of impurities present, the amount of material to be purified, the column dimensions, etc. Such conditions are readily determined on a case by case basis by those of ordinary skill in the art.

Assessment of the MHC-Peptide Complex

The complexes of the invention can be assayed using an in vitro system or using an in vivo model. In the in vitro system, the complex is incubated with peripheral blood T cells from subjects immunized with, or showing immunity to, the protein or antigen responsible for the condition associated with the peptide of the complex. The successful complex will induce anergy in syngeneic T cells and prevent proliferation of the T cells even upon stimulation with additional antigen.

In the in vivo system, T cells that proliferate in response to the isolated epitope or to the full length antigen in the presence of APC are cloned. The clones are injected into histocompatible animals which have not been immunized in order to induce the autoimmune disease. Symptoms related to the relevant complex should ameliorate or eliminate the symptoms of the disease.

Either of the types of complexes, i.e., with or without the effector component, may be used. In one mode the treatment is two-fold. The individual is treated with the complex of MHC-encoded antigen-presenting glycoprotein containing an effective portion of the antigen to down-regulate the immune system. Further down-regulation is achieved by treatment with the three component complex with includes the MHC-encoded antigen-presenting glycoprotein, an effective portion of antigen which is specific for the autoimmune disease being treated, and an effector component. In addition, panels of complexes may be used for treatment. For example, if it is suspected that more than one peptide of an antigen is involved in the autoimmune response, and/or if it is suspected that more than one antigen is involved, the individual may be treated with several complexes selected from a panel containing the effective portion of the appropriate MHC-encoded antigen-presenting polypeptides, and effective portions of antigens; these may be with or without effector components.

Administration of a labeled complex permits identification of those portions of the immune system involved in the disease, in diagnostic applications.

Selection of the MHC-Peptide Complexes for Therapy and/or Diagnosis

In order to select the MHC complexes of the invention which are to be used in the diagnosis or treatment of an individual for an autoimmune disease, the type of MHC antigens which are involved in the presentation of the autoantigen are identified.

Specific autoimmune dysfunctions are correlated with specific MHC types. A list of the DQ/DR haplotypes in humans and their associations with autoimmune diseases are shown in FIG. 2. Methods for identifying which alleles, and subsequently which MHC encoded polypeptides, are associated with an autoimmune disease are known in the art. A method described in EP 286447 is suitable. In this method, several steps are followed. First, the association between an MHC antigen and the autoimmune disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease (See, FIG. 2).

Second, specific alleles encoding the disease associated with MHC antigen/polypeptide are identified. In the identification of the alleles, it is assumed that the susceptibility allele is dominant. Identification of the allele is accomplished by determining the strong positive association of a specific subtype with the disease. This may be accomplished in a number of ways, all of which are known to those skilled in the art. Subtyping may be accomplished, for example, by mixed lymphocyte response (MLR) typing or by primed lymphocyte testing (PLT). Both methods are described in Weir and Blackwell (eds.), *Handbook of Experimental Immunology*, which is incorporated herein by reference. It may also be accomplished by analyzing DNA restriction fragment length polymorphism (RFLP) using DNA probes that are specific for the MHC locus being examined. See, e.g., Nepom, *Annals N.Y. Acad. Sci.* 475:1 (1986). Methods for preparing probes for the MHC loci are known to those skilled in the art. See, e.g.,, Gregersen. et al., *Proc. Natl. Acad. Sci. USA* 79:5966 (1986); Weissman, et al., in Medicine in Transition: the Centennial of the University of Illinois College of Medicine (E. P. Cohen, ed. 1981), all of which are incorporated herein by reference.

The most complete identification of subtypes conferring disease susceptibility is accomplished by sequencing of genomic DNA of the locus, or cDNA to mRNA encoded within the locus. The DNA which is sequenced includes the section encoding the hypervariable regions of the MHC encoded polypeptide. Techniques for identifying specifically desired DNA with a probe and for amplification of the desired region are known in the art, and include, for example, the polymerase chain reaction (PCR) technique.

Once the allele which confers susceptibility to the specific autoimmune disease is identified, the polypeptide encoded within the allele is also identifiable, i.e., the polypeptide sequence may be deduced from the sequence of DNA within the allele encoding it. The MHC antigen complexes of the invention used for diagnosis and/or for therapy are derived from the effective portion of the MHC antigen associated with the autoimmune disease state and from an autoimmune antigen associated with the same disease state.

As an example, over 90% of rheumatoid arthritis patients have a haplotype of DR4(Dw4), DR4(Dwl4) or DR1 (See, FIG. 2). It is also known that a target antigen in human rheumatoid arthritis is type-II collagen. Hence, the complexes of the invention used for treatment or diagnosis of an individual with rheumatoid arthritis would include those containing a polypeptide derived from the DR4(Dw4), DR1 and/or DR4(Dwl4) which is capable of antigen presentation for disease induction, or which is incapable of antigen presentation for disease suppression, complexed with an effective portion of type-II collagen.

A protocol which may be suitable for the utilization of the complexes of the invention for the diagnosis and/or treatment of an autoimmune disease is depicted in FIG. 3. Briefly, an individual having (or susceptible to) an autoimmune disease is identified, and the autoimmune dysfunction is identified. Identification may be by symptomology and/or an examination of family histories. The individual's MHC type is determined by one or more of several methods known in the art, including, for example, cell typing by MLR, by serologic assay, and by DNA analysis (including RFLP and PCR techniques). The individual's T cells are examined in vitro, to determine the autopeptide(s) recognized by autoreactive T cells; this is accomplished utilizing labeled complexes of the invention, described above. After it is determined which complexes target the T cells, the individual is treated with complexes that are able to induce anergy in the specific autoreactive T cell replication and/or with complexes that kill the autoreactive T cells. Therapy (as determined by the autoreactive T cells remaining) is monitored with T cell binding studies using the labeled complexes of the invention, described supra.

As used herein, the term "individual" encompasses all mammals and all vertebrates which possess basically equivalent MHC systems.

Formulation and Administration of the MHC-Peptide Complex

If the transmembrane region of the MHC subunit is included, these complexes are conveniently administered after being incorporated into lipid monolayers or bilayers. Typically, liposomes are used for this purpose, but any form of lipid membrane, such as planar lipid membranes or the cell membrane of a cell (e.g., a red blood cell) may be used. The complexes are also conveniently incorporated into micelles. It has been determined that MHC-peptide complexes comprising dimeric MHC molecules exist primarily as aggregates.

Liposomes can be prepared according to standard methods, as described below. However, if the transmembrane region is deleted, the complex can be administered in a manner conventionally used for peptide-containing pharmaceuticals.

Administration is systemic and is effected by injection, preferably intravenous. Formulations compatible with the injection route of administration may, therefore, be used. Suitable formulations are found in *Remington's Pharmaceutical Sciences,* (Mack Publishing Company, Philadelphia, Pa., 17th ed. (1985)), which is incorporated herein by reference. A variety of pharmaceutical compositions comprising complexes of the present invention and pharmaceutically effective carriers can be prepared. The pharmaceutical compositions are suitable in a variety of drug delivery systems. For a brief review of present methods of drug delivery, see, e.g., Langer, *Science* 249:1527–1533 (1990) which is incorporated herein by reference.

In preparing pharmaceutical compositions comprising MHC-peptide complexes, it is frequently desirable to modify the complexes to alter their pharmacokinetics and biodistribution. For a general discussion of pharmacokinetics, see, *Remington's Pharmaceutical Sciences,* supra, Chapters 37–39. A number of methods for altering pharmacokinetics and biodistribution are known to one of ordinary skill in the art (see, e.g., Langer, supra). For instance, methods suitable for increasing serum half-life of the complexes include treatment to remove carbohydrates which are involved in the elimination of the complexes from the bloodstream. Preferably, all of the carbohydrate moieties are substantially removed by the treatment. All of the carbohydrate moieties are considered to be substantially removed if at least about 75%, preferably about 90%, and most preferably about 99% of the carbohydrate moieties are removed. Conjugation to soluble macromolecules, such as proteins, polysaccharides, or synthetic polymers, such as polyethylene glycol, is also effective. Other methods include protection of the complexes in vesicles composed of substances such as proteins, lipids (for example, liposomes), carbohydrates, or synthetic polymers.

Liposomes of the present invention typically contain the MHC-peptide complexes positioned on the surface of the liposome in such a manner that the complexes are available for interaction with the T cell receptor. The transmembrane region is usually first incorporated into the membrane at the time of forming the membrane. The liposomes can be used to target desired drugs (e.g., toxins or chemotherapeutic agents) to particular autoreactive T cells. Alternatively, the complexes embedded in the liposome may be used to induce anergy in the targeted cells.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for therapeutic and diagnostic uses. For instance, liposomes which can be maintained from 8, 12, or up to 24 hours in the bloodstream are particularly preferred.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serve to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4,837,028, incorporated herein by reference.

Additionally, the liposome suspension may include lipid-protective agents which protect lipids against free-radical and lipid-peroxidative damages on storage. Lipophilic free-radical quenchers, such as atocopherol and water-soluble iron-specific chelators, such as ferrioxianine, are preferred.

A variety of methods are available for preparing liposomes, as described in, for example, Szoka, et al., *Ann. Rev. Biophys. Bioeng.* 9:467 (1980), and U.S. Pat. Nos. 4,235,871, 4,501,728 and 4,837,028, all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powderlike form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration which is desired in the interior volume of the liposomes in the final liposome suspension. Typically, the drug solution contains between about 10 to about 100 mg/ml of the complexes in a buffered saline solution.

Following liposome preparation, the liposomes may be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposome to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-bearm particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more complex in a free (nonencapsulated) form.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a replacement medium. Alternatively, gel filtration can be used to separate large liposome particles from solute molecules.

Following the above treatment, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposomes comprising the MHC-peptide complex may be administered parenterally or locally in a dose which varies according to, e.g., the manner of administration, the drug being delivered, the particular disease being treated, etc.

Micelles are commonly used in the art to increase solubility of molecules having nonpolar regions. One of skill will thus recognize that micelles are useful in compositions of the present invention. Micelles comprising the complexes of the invention are prepared according to methods well known in the art (see, e.g., Remington's *Pharmaceutical Sciences,* supra, Chap. 20). Micelles comprising the complexes of the present invention are typically prepared using standard surfactants or detergents.

Micelles are formed by surfactants (i.e., molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell, whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethlene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. For surfactants whose hydrocarbon portion is a single normal alkyl chain, the maximum aggregation numbers consistent with spherical shape are approximately 27, 39, 54, 72, and 92 for $C_8$, $C_{10}$, $C_{12}$, $C_{14}$ and $C_{16}$, respectively. If the surfactant concentration is increased beyond a few percent and if electrolytes are added (in the case of ionic surfactants) or the temperature is raised (in the case of nonionic surfactants), the mircelles increase in size. Under these conditions, the micelles are too large to remain spherical and become ellipsoidal, cylindrical or finally lamellar in shape.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127˚(Wyandotte Chemicals Corp.). Preferred surfactants are nonionic polyoxyethylene and polyoxypropylene detergents compatible with IV injection such as, TWEEN-80˚, PLURONIC F-68˚, n-octyl-β-D-glucopyranoside, and the like. In addition, phospholipids, such as those described for use in the production of liposomes, may also be used for micelle formation.

Since the MHC subunits of the present invention comprise a lipophilic transmembrane region and a relatively hydrophilic extracellular domain, mixed micelles are formed in the presence of common surfactants or phospholipids and the subunits. The mixed micelles may comprise any combination of the subunits, phospholipids and/or surfactants. Thus, the micelles may comprise subunits and detergent, subunits in combination with both phospholipids and detergent, or subunits and phospholipid.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. Dosage levels for murine subjects are generally between about 10 $\mu$g and about 500 $\mu$g. A total dose of between about 50 $\mu$g and about 300 $\mu$g is preferred. For instance, in treatments provided over the course of a disease, three 25 $\mu$g or 100 $\mu$g doses are effective. Total dosages range between about 0.015 and about 15 $\mu$g/kg, preferably about 0.15 to about 10 $\mu$g/kg.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, compositions for intravenous administration are provided which comprise a solution of the complex dissolved or suspended in an acceptable carrier, preferably an aqueous carrier. A variety of aqueous carriers may be used, e.g., water, buffered water, 0.4% saline, and the like. For instance, phosphate buffered saline (PBS) is particularly suitable for administration of soluble complexes of the present invention. A preferred formulation is PBS containing 0.02% TWEEN-80. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. Preferred concentrations for intravenous administration are about 0.02% to about 0.1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant- The surfactant must, of course, be nontoxic, and preferably soluble in the propellant. Representative of such agents are the esters or partial esters of fatty acids containing from 6 to 22 carbon atoms, such as, for example, caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, compositions containing the complexes of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

In diagnostic applications, compositions containing the appropriately complexes or a cocktail thereof are administered to a patient suspected of having an autoimmune disease state to determine the presence of autoreactive T cells associated with the disease. Alternatively, the efficacy of a particular treatment can be monitored. An amount sufficient to accomplish this is defined to be a "diagnostically effective dose." In this use, the precise amounts will depend upon the patient's state of health and the like, but generally range from 0.01 to 1000 mg per dose, especially about 10 to about 100 mg per patient.

Kits can also be supplied for therapeutic or diagnostic uses. Thus, the subject composition of the present invention may be provided, usually in a lyophilized form in a container. The complexes, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration. Frequently, it will be desirable to include an inert extender or excipient to dilute the active ingredients, where the excipient may be present in from about 1 to 99% wt. of the total composition. Where an antibody capable of binding to the complex is employed in an assay, this will usually be present in a separate vial. The antibody is typically conjugated to a label and formulated according to techniques well known in the art.

This invention will be described in greater detail by way of specific examples. The following examples are offered for illustrative purposes, and is intended neither to limit or define the invention in any manner.

EXAMPLES

I. MATERIALS AND GENERAL PROTOCOLS

A. Cell Lines, Antibodies and Chemicals

The hybridoma cell line L243, producing monoclonal antibodies against monomorphic human HLA DR molecules was obtained from American Type Culture Collection, Bethesda, Md. Homozygous lymphoblastoid cell line GM 03107 expressing HLA-DR2 was obtained from the National Institute of General Medical Sciences (NIGMS), human genetic mutant cell repository (Coriell Institute of Medical Research, NJ). Human DT T cell line restricted for HLA-DR2 and [6×His-MBP(84-102)$Y^{83}$] was generated at Anergen, Inc. $Ni^{2+}$•NTA resin was purchased from Qiagen, CA. Ampholines and various isoelectric point markers for two-dimensional electrophoresis were purchased from Bio-Rad Laboratories.

B. Purification of Human HLA-DR2 From Lymphoblastoid Cells

EBV-transformed lymphoblastoid cells were cultured in RPMI 1640 medium containing 2 mM L-glutamine and 10% heat inactivated FBS, and were harvested at a cell density of $1 \times 10^6$ cells/ml. HLA-DR2 was purified from Triton X-100 membrane extracts of cultured GM 03107 lymphoblastoid cells on L243 monoclonal antibody-coupled Sepharose 4B column. Purification of monoclonal antibody and coupling to CNBr-activated Sepharose 4B was carried out as described earlier (see, Nag, et al., *J. Immunol. Methods*, 142:105 (1991); and Nag, et al., *J. Immunol.*, 148:369 (1992)). Purification of HLA-DR2 was carried out as described earlier (see, Nag, et al., *J. Immunol.*, 150:1358 (1993)) with some modifications. Briefly, a high speed (100,000×g) membrane fraction was detergent extracted in a buffer containing 10 mM Tris-HCl, pH 8.3, 0.5% Triton X-100, 0.1M NaCl, 5 mM EDTA, 0.02% sodium azide and 1 mM PMSF. The lysate was recycled over the antibody column (pre-equilibrated with the same buffer) at 4° C. for 16 h. The column was washed with ten bed volumes of phosphate-buffered saline (PBS) containing 0.5% Triton X-100, 0.02% sodium azide and 1 mM PMSF followed by five bed volumes of PBS containing 0.01% Tween-80 detergent. Finally, the HLA-DR2 mix was eluted with 20 mM phosphate buffer, pH 11, containing 0.1M NaCl, 0.01% Tween-80 and 0.02% sodium azide. Each fraction was neutralized with 1M acetic acid to a final concentration of 12 mM, and the protein solution was concentrated using an Amicon Centriprep-10 concentrator. Affinity-purified class II antigens were characterized by 13.5% SDS polyacrylamide gel electrophoresis following silver staining.

C. Synthesis of Peptides

The peptide analog of MBP(84-102) containing six histidine residues at the N-terminus followed by a tyrosine residue for radiolabeling [6×His-MBP(83-102)$Y^{83}$] peptide with the sequence HHHHHHYDPVVHFFKNIVTPRTPPPS (Sequence I.D. No. 2), the [MBP(83-102)$Y^{83}$] peptide with the sequence YDPVVHFFKNWThRTPPPS (Sequence I.D. No. 3) and MBP(124-143) peptide with the sequence GFGYGGRASDYKSAHKGFKG (Sequence I.D. No. 4) were synthesized by the standard solid phase method using side-chain protected FMOC amino acids on an Applied Biosystems 431A automated peptide synthesizer. The deprotected, crude peptides were purified by reverse-phase HPLC, and the homogeneity and identity of the purified peptides were confirmed by mass spectroscopic analysis.

D. Radiolabeling of Peptides

Radiolabeling of peptides was achieved by the standard chloramine-T labeling procedure (Hunter and Greenwood, *Nature*, 194:495 (1962)). Typically, 1.0 mg of peptide in 0.5 ml volume was incubated with 1.0 mCi of Na-$^{125}$I in 0.1M sodium phosphate buffer, pH 7.7. The labeled peptides were separated from free $^{125}$I by Sephadex G-10 gel filtration chromatography. Specific activities of various MBP peptides ranged from $3.6 \times 10^5$ to $3.5 \times 10^7$ cpm/$\mu$g.

E. Complex Preparation and Peptide Binding Assay

Affinity-purified HLA-DR2 at a concentration of 200 $\mu$g/ml was incubated with 10- or 50-fold molar excess of radiolabeled [6×His-MBP(83-102)$Y^{83}$] peptide or [MBP(83-102)$Y^{83}$] peptide at 37° C. for 96 h at pH 7.0. Resulting complexes were analyzed by 12.0 or 13.5% SDS polyacrylamide gel electrophoresis under non-reduced conditions. Gels were silver stained, dried and autoradiographed. Each lane containing the $\alpha/\beta$ heterodimer as well as partially dissociated $\alpha$ and $\beta$ chains was cut out from the dried gel and counted in a LKB 1261 multigamma counter. The percent of DR antigens with bound peptide was then calculated from the specific activity of the respective peptide.

F. $Ni^{2+}$•NTA Chelate Affinity Chromatography

Prior to the $Ni^{2+}$•NTA affinity chromatography, complexes of HLA-DR2 and radiolabeled [6×His-MBP(83-102)$Y^{83}$] peptide were dialyzed extensively against PBS containing 0.01% Tween-80 and 0.02% sodium azide to remove unbound peptide. Complex preparations were then passed through preoptimized Sephadex G-75 column to ensure complete removal of free peptide. Purified radiolabeled complexes were then incubated with $Ni^{2+}$•NTA resin (1 ml) at room temperature for 2 h on a shaker in the presence of 10 mM imidazole. The resin was then transferred into a small disposable column and washed with PBS containing 0.01% Tween-80 and 0.02% sodium azide until the base line was achieved. The bound complexes were finally eluted in the presence of 80 mM imidazole. Fractions of 200 $\mu$L were collected and counted in a multigamma counter for detecting the elution profile. The peak containing the complexes of HLA-DR2 and [6×His-MBP(83-102)$Y^{83}$] peptide was pooled and the protein concentration was determined by Lowry assay. Milligram quantities of unlabeled complexes of HLA-DR2 and [6×His-MBP(83-102)$Y^{33}$] peptide were prepared similarly and the elution profile was monitored by measuring absorbancy at 280 nm.

G. Acid Extraction of Bound Peptides and Narrowbore HPLC Analysis

Extraction of bound peptides from complexes of HLA-DR2 and MBP peptide was carried out as described earlier (see, Chicz, et al., *Nature*, 358:764 (1992)) with some minor modifications. Briefly, 780 $\mu$g of purified complexes of HLA-DR2•[6×His-MBP(83-102)$Y^{83}$] at a concentration of 1 mg/ml before and after $Ni^{2+}$•NTA chromatography was incubated at 70° C. for 15 min with equal volume of 20% acetic acid. The reaction mixture was centrifuged and the peptide pool supernatant was collected, frozen to –80° C. and lyophilized. Reverse-phase high performance liquid chromatography (HPLC) was performed on a Waters (Millipore) 590 model using C-18 (0.21×15 cm) Vydac 218TP5215 narrowbore column with a linear gradient of increasing acetonitrile from 10–60% in 0.1% trifluoroacetic acid (TFA). Acid-eluted HPLC peptide peak from post-$Ni^{2+}$•NTA complexes was collected and lyophilized, and the identity was confirmed by integrated microsequencing using Porton PI2090 sequencer.

H. Two-Dimensional Gel Electrophoresis

The method described earlier by O'Farrell and Goodman (see, *Cell*, 9:289 (1976)) was used with some modifications to separate the polypeptides according to their charge in the first dimension (IEF) and then according to their size in the second dimension. Briefly, the first dimensional gels were poured to a height of 6.5 cm in a glass tube (1 mm inner diameter×7.5 cm length). The gel solution contained 9.2M urea, 5.5% acryl-amide/bis, 2% Triton X-l00 and a mixture of 1.5% ampholines (pH 5–7) and 0.5% ampholines (pH 3–10) which was degassed and polymerized by adding 50 $\mu$L of 10% ammonium persulfate and 18 $\mu$L of N,N,N',N'-tetramethylethylenediamine (TEM-ED) per 10 ml of gel mixture. Purified HLA-DR2 and post $Ni^{2+}$•NTA complexes were concentrated by acetone precipitation, resuspended in sample buffer (9.5M urea, 2.0% Triton X-100, 150 mM DTT and a mixture of 1.5% ampholines (pH 5–7) and 0.5% ampholines (pH 3–10)) and incubated at 37° C. for 18 h. 5 $\mu$g of each sample was loaded in the tube gels and overlayed with 8 $\mu$L of 2D standards (Bio-Rad Laboratories). 30 $\mu$L of sample overlay solution (9M urea, 1% ampholines (pH 5–7), 0.5% ampholines (pH 3–10) and 0.05% bromophenol blue) was used to overlay the sample solution. The IEF electrophoresis was carried out at 900 V for 3.5 h. The lower chamber buffer contained 10 mM phosphoric acid and the upper chamber contained 20 mM sodium hydroxide. After completion of the first dimensional run, the gels were removed and placed on top of a 13.5% polyacrylamide-SDS gel containing a 4.5% stacking gel in a Bio-Rad minigel assembly. The IEF tube gels were incubated for 5 min with reducing sample buffer (62.5 mM Tris HCl, pH 6.8, 10% glycerol, 2% SDS and 25 mM DTT and 0.05% bromophenol blue), preheated to 95° C. for 5 min and electrophoresed at a constant current of 50 mA for 2 min followed by 25 mA for 45 min. Gels were stained with silver for analysis.

I. T cell proliferation assay

The DT T cell line (20 days following antigen pulsing) was purified from residual APCs by subjecting them to a 19% metrizamide density gradient centrifugation, followed by two washes in RPMI 1640 medium. $2 \times 10^4$ T cells were cultured in triplicate with $5 \times 10^5$ freshly irradiated autologous APCs in the presence of increasing concentrations of various peptides. During the final 8 h of a 72 h incubation at 37° C., 1 $\mu$Ci of [$^3$H]thymidine was added and the degree of proliferation was measured by incorporated radioactivity.

II. EXPERIMENTAL FINDINGS

In vitro incubation of affinity-purified MHC class II molecules with various synthetic antigenic peptides results in only a small fraction of the MHC molecules being complexed by a specific peptide (O'Sullivan, et al., *J. Immunol.*, 145:1799 (1990); Nag, et al., supra, 1992). The majority of purified class II antigens, however, are occupied with either prebound endogenous peptides or invariant chains. As a result, the percent of MHC class II molecules occupied with a given peptide varies significantly. Due to the low peptide occupancy and significant variations in peptide binding of a given MHC class II with different peptides, preparation of homogeneous complexes of class II-peptide have been technically infeasible. As previously mentioned, a biotin-avidin system has been described where peptides were appropriately modified to eliminate side reactions and then conjugated with a long-chain thiol cleavable biotinylated reagent (Demotz, et al., *Proc. Natl. Acad. Sci. USA*, 88:8730 (1991)). This allowed specific retention of particular MHC peptide complexes to an avidin column. However, the purified complexes by this method resulted in only 0.4–4% recovery of starting samples.

The present invention provides a method of preparing MHC-peptide complexes of known composition by taking advantage of metal ion chelate affinity chromatography. Affinity-purified HLA-DR2 and a peptide analog of myelin basic protein MBP(84-102) are used to demonstrate the utility and superiority of the presently claimed method. The transformed lymphoblastoid cell line GM 03107 used to purify class II antigens express HLA-DR2. The MBP epitope selected for this study has been shown previously to bind HLA-DR2 with high affinity (Valli, et al., *J. Clin. Invest.*, 91:616 (1993)), and is considered as a major autoimmune epitope for multiple sclerosis (Ota, et al., *Nature*, 346:183 (1990)), a demyelinating autoimmune disease of central nervous system. For metal ion affinity, 6 histidine residues were added at the N-terminus end of this peptide. In addition, a tyrosine residue was added following the 6xHis tag to enable radiolabeling with $^{125}$I.

Figure 4A:
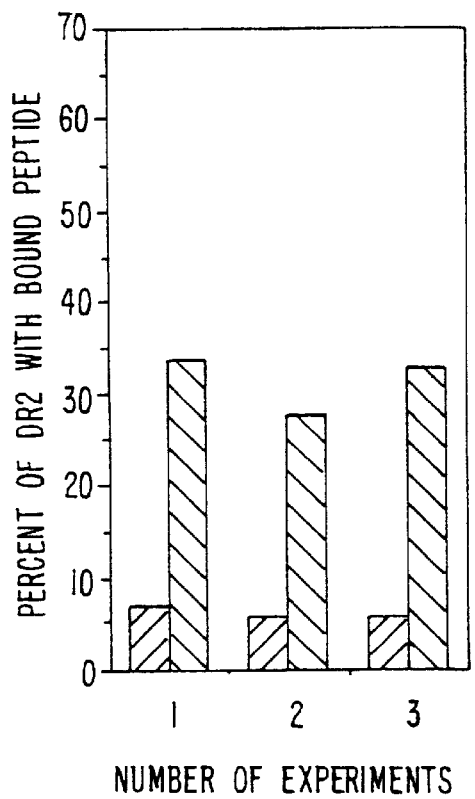
FIG. 4 shows the binding of the [MBP(83-102)$Y^{83}$] and [6×His-MBP(83-102)$Y^{83}$] peptides to HLA-DR2. Purified mixture of HLA-DR2 at a concentration of 0.2 mg/ml was incubated with either 10-fold (A) or 50-fold (B) molar excess of each peptide and resulting complexes were analyzed by 13.5% polyacrylamide gel electrophoresis. Solid bars represent the binding of [6×His-MBP(83-102)$Y^{83}$] peptide and shaded bars represent the binding of [MBP(83-102)$Y^{83}$] peptide to HLA-DR2. Specific activity of various MBP peptides ranged as: $3.6\times10^5$–$3.5\times10^7$ cpm/μg for [6×His-MBP(83-102)$Y^{83}$] peptide and $1.7\times10^5$–$1.03\times10^6$ cpm/μg for [MBP(83-102)$^{83}$] peptide. The figure represents data obtained from three separate experiments.
Figure 4B:
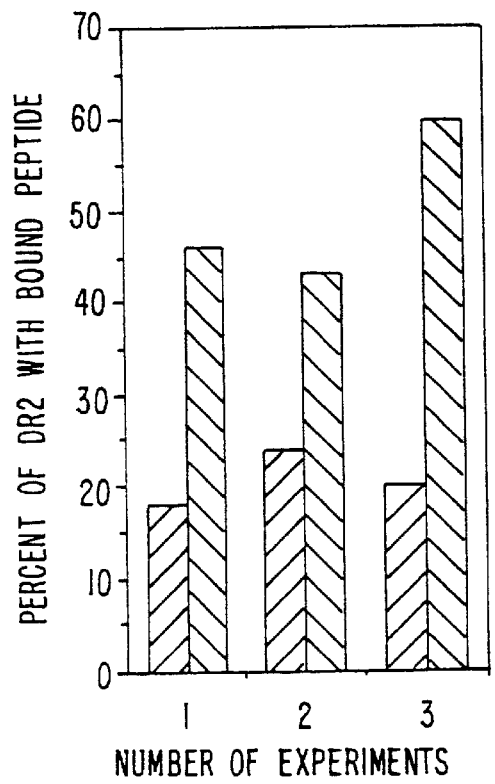

HLA-DR2 antigens were purified from lymphoblastoid cells on an antibody-coupled affinity column. The silver staining of purified proteins showed that purity was greater than 98%. The binding of the MBP peptide analog [6xHis-MBP(83-102)$Y^{83}$] with purified HLA-DR2 was compared with non-histidine containing [MBP(83-102)$Y^{83}$] peptide at two different concentrations. The peptide binding was measured by SDS polyacrylamide gel electrophoresis under non-reduced conditions. An equivalent amount of radiolabeled peptide incubated under identical conditions, but in the absence of HLA-DR2 was used as a control. The conditions for maximum peptide occupancy of HLA-DR2 with MBP peptides were optimized and found to be 96 h at 37° C. with a 50-fold molar excess of peptide at pH 7.0. Results presented in FIG. 4 show that both MBP peptides were able to bind HLA-DR2. When the affinity of binding was compared, the 6xHis tagged peptide showed increased binding to HLA-DR2 than non-histidine tagged peptide at both 10- and 50-fold excess peptide concentrations (FIGS. 4A and 4B). This is not surprising, since in the case of many purified 6xHis-tagged proteins and enzymes, an increased specific activity was observed as compared to non-histidine tagged molecules. Furthermore, the recent three-dimensional crystal structure of MHC class II molecules showed that the peptide binding site is open at both ends and, in contrast to MHC class I molecules where mostly 9-mers bound strongly, longer peptides are seen to be bound with increased affinity in an extended conformation (Brown, et al., *Nature*, 364:33 (1993)).

Figure 5A:
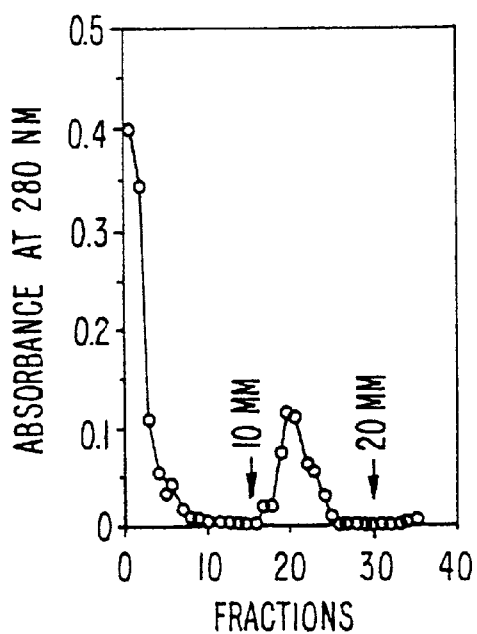
FIG. 5 shows the optimization of $Ni^{2+}$•NTA affinity chromatography. Optimization of $Ni^{2+}$•NTA chromatography where only [6×His-MBP(83-102)$Y^{83}$] peptide but not HLA-DR2 bound to the resin was carried out with non-radiolabeled mixture of HLA-DR2 and [6×His-MBP(83-102)$Y^{83}$] peptide. A: represents the binding of HLA-DR2 to the resin in the absence of imidazole where 500 μg of HLA-DR2 mixture was incubated with 0.2 ml resins in PBS containing 0.01% Tween-80 and 0.02% azide. B: represents the binding of 500 μg HLA-DR2 to 0.5 ml resin in the presence of PBS containing 0.01% Tween-80, 0.02% azide and 10 mM imidazole. C: represents the binding of 2.0 mg of [6×His-MBP(83-102)$Y^{83}$] peptide to 0.5 ml $Ni^{2+}$•NTA resin in the presence of PBS containing 0.01% Tween-80, 0.02% azide and 10 mM imidazole. Fractions of 200 μl were collected and absorbance was measured at 280 nm. Arrows in each panel represent various imidazole concentrations used for the elution of either HLA-DR2 or [6×His-MBP(83-102)$Y^{83}$] peptide.
Figure 5B:
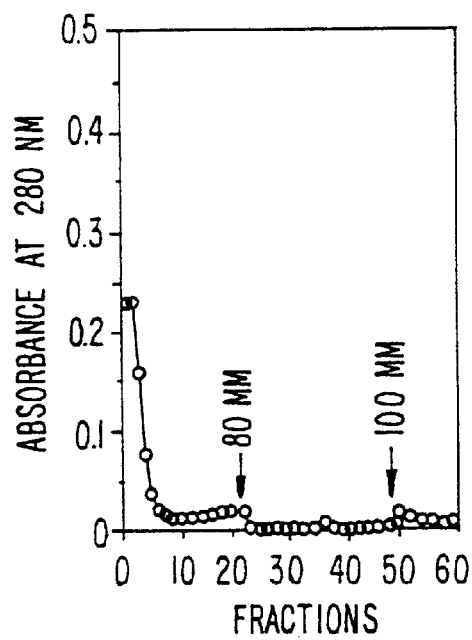
Figure 5C:
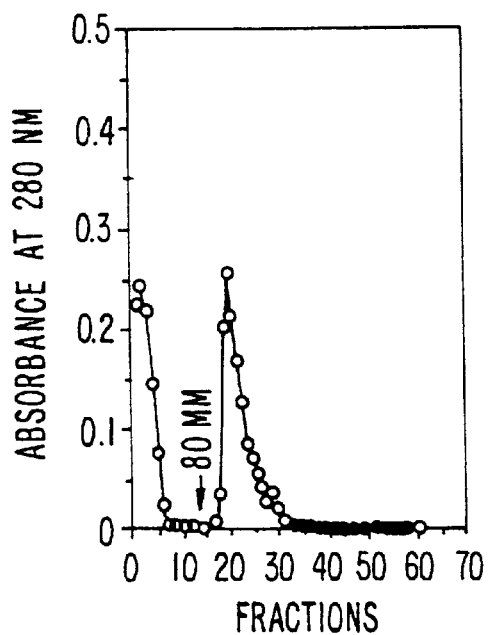

The conditions for $Ni^{2+}$•NTA chromatography were next optimized where HLA-DR2 showed no binding to the $Ni^{2+}$•NTA resin. This was essential as both α and β chains of HLA-DR2 contain several histidine residues, respectively (Lee, et al., *Nature*, 299:750 (1982); Lee, et al., *Proc. Natl. Acad. Sci. USA*, 84:4591 (1987)). Furthermore, among various histidine residues in the β chain, two at positions 160 and 161 are present adjacent to each other. As shown in FIG. 5A, HLA-DR2 alone can bind to the $Ni^{2+}$•NTA resin. However, the affinity of the binding of purified HLA-DR2 to $Ni^{2+}$•NTA resin was relatively low as all of the bound HLA-DR2 antigens can be eluted at an imidazole concentration of 10 mM. Further increase in the imidazole concentration beyond 10 mM imidazole did not show any detectable HLA-DR2. This was also confirmed by incubating HLA-DR2 mixture with the $Ni^{2+}$•NTA resin in the presence of 10 mM imidazole-containing buffer. As shown in FIG. 5B, under this condition no binding of HLA-DR2 to $Ni^{2+}$•NTA was observed. In contrast, since the affinity of the $Ni^{2+}$•NTA resin for the 6xHis-tag is much higher, the [6xHis-MBP(83-102)$Y^{83}$] peptide was fully capable of binding to the resin in the presence of 10 mM imidazole. The affinity of the 6xHis-tagged peptides or proteins to $Ni^{2+}$•NTA resin has been reported to be higher than the average affinity of antigens for antibodies or enzymes for substrates, with a $K_d$ of $10^{-13}$ at pH 8.0. The complete elution of 6xHis-tag peptide in the present case required 80 mM imidazole concentration (see, FIG. 5C). No detectable amount of peptide was recovered from the resin by increasing the imidazole concentration beyond 80 mM.

Figure 6A:
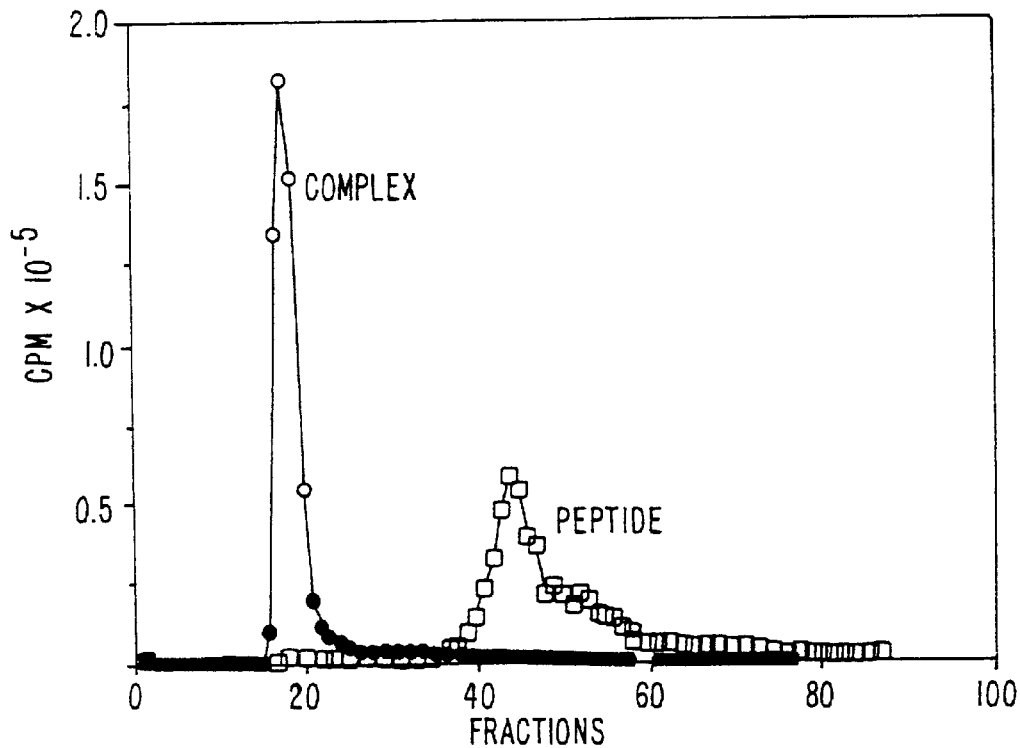
FIG. 6 shows a sephadex G-75 gel filtration and purification of complexes containing HLA-DR2 and [6×His-MBP(83-102)$Y^{83}$] peptide by $Ni^{2+}$•NTA chromatography. To ensure the complete removal of residual free [6×His-MBP(83-102)$Y^{83}$] peptide following the dialysis of the radiolabeled complexes, Sephadex G-75 gel filtration chromatography was performed. A: represents size-exclusion resolution of radiolabeled complexes from labeled [6×His-MBP(83-102)$Y^{83}$] peptide. 1 μg of dialyzed radiolabeled complexes and 1 ng of labeled peptide was applied on a 25 cm×1 cm Sephadex G-75 column (bed volume 10 ml) in a total volume of 200 μl. The column was pre-equilibrated in PBS containing 0.01% Tween-80 and 0.02% azide and fractions of 0.2 ml was collected with a flow rate of 0.1 ml/min. Each fraction was counted for radioactivity content. The purified complexes were then incubated with $Ni^{2+}$•NTA resin. B: represents an elution profile of radiolabeled complexes (150 μg) from $Ni^{2+}$•NTA column (●). In a mock experiment, 50-fold molar excess amount of radiolabeled [6×His-MBP(83-102)$Y^{83}$] peptide (443 μg, spec. act. 2.9× $10^6$ cpm/μg) was incubated in the absence of class II antigens, dialyzed under identical conditions and passed through $Ni^{2+}$•NTA column (○). The inset figure in (B) represents silica gel TLC analysis of both mock and complexes of HLA-DR2 and [6×His-MBP(83-102)$Y^{83}$] peptide.
Figure 6B:
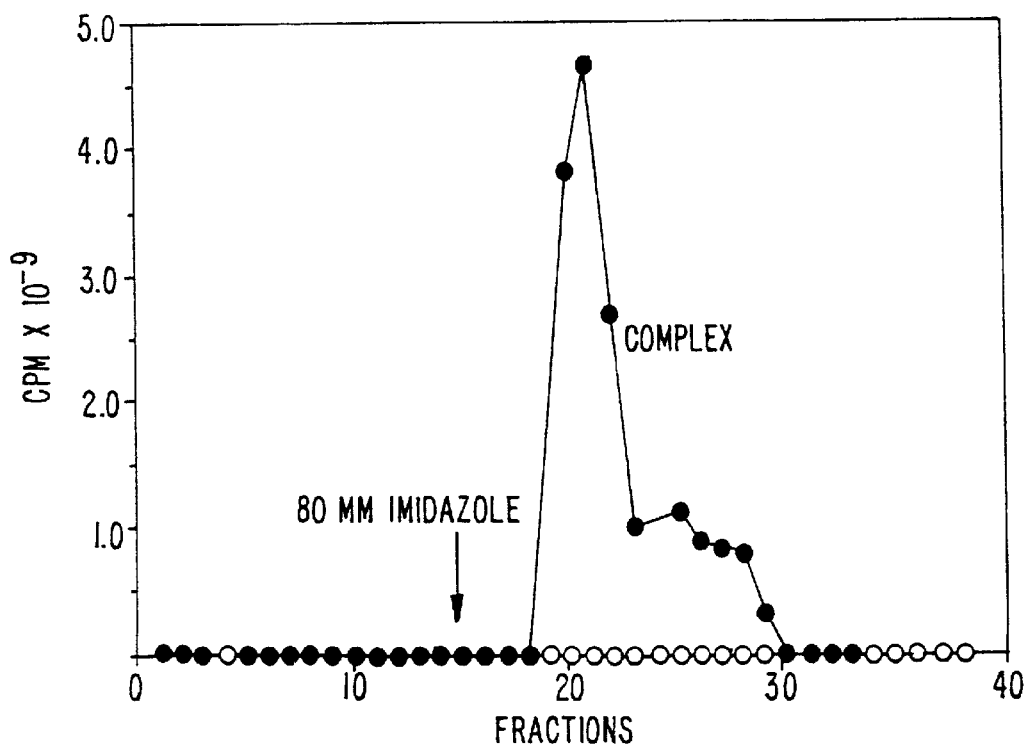

Following the optimization of conditions for peptide binding to $Ni^{2+}$•NTA resin, complexes of HLA-DR2 with radiolabeled [6xHis-MBP(83-102)$Y^{83}$] were prepared and purified. Since free [6xHis-MBP(83-102)$Y^{83}$] peptide has a strong affinity for the resin, complete removal of unbound peptide was essential prior to the affinity chromatography. This was accomplished by extensive dialysis of the complex preparations followed by gel filtration chromatography. Since every peptide is not easily dialyzable, the size-exclusion chromatography is an essential step to ensure complete removal of unbound peptides. Among various gel filtration resins, Sephadex G-75 gave the best resolution of [6xHis-MBP(83-102)$Y^{83}$] peptide from complexes (FIG. 6A). In the case of [6xHis-MBP(83-102)$Y^{83}$] peptide, however, the dialysis step alone was sufficient to remove unbound peptide. This is shown in a control experiment, where an equivalent amount of peptide incubated in the absence of HLA-DR2 antigens and dialyzed did not show binding to the $Ni^{2+}$•NTA resin (FIG. 6B, open circles). The complete removal of residual radiolabeled [6xHis-MBP(83-102)$Y^{83}$] peptide can also be demonstrated by silica gel TLC plate assay as described earlier (Nag, et al., supra, 1991; Nag, et al., supra, 1992). Peptide-free complexes were than incubated with $Ni^{2+}$•NTA resin and bound complexes were eluted in the presence of 80 mM imidazole (FIG. 6B). The calculation of the percent of HLA-DR2 bound with labeled peptide in the 80 mM imidazole-eluted peak of three such experiments showed an average of 107% (±4.5%) occupancy of HLA- DR2 with the [6xHis-MBP(83-102)$Y^{83}$] peptide. The recovery of complexes after $Ni^{2+}$•NTA chromatography was estimated to be 49–74% of the total peptide bound HLA-DR2 in three different experiments and are summarized in Table 1.

TABLE 1

Percent of HLA-DR2 Occupied With [6 X His-MBP(83-102)$Y^{83}$] Peptide Before and After $Ni^{2+}$.NTA Affinity Chromatography

| Total protein (μg) | Concentration (mg/ml) | Molar excess peptide | Percent Occupancy before (%) $Ni^{2+}$.NTA | Percent Occupancy after (%) $Ni^{2+}$.NTA | Percent Recovery (%) |
|---|---|---|---|---|---|
| 100 | 0.198 | 50 | 34.0 | 112.0 | 60.0 |
| 100 | 0.198 | 50 | 46.0 | 103.0 | 49.0 |
| 150 | 0.150 | 50 | 27.0 | 108.0 | 74.0 |

The percent of HLA-DR2 with bound labeled peptide was calculated from the specific activity of $^{125}$I-labeled [6 X His-MBP(83-102)y$^{83}$] peptide. Protein concentrations in eluted peaks were determined by Lowry assay. The percent recovery was calculated from the amount of complexes containing HLA-DR2 and [6 X His-MBP(83-102)$Y^{83}$] peptide before and after $Ni^{2+}$.NTA chromatography.

Figure 7A:
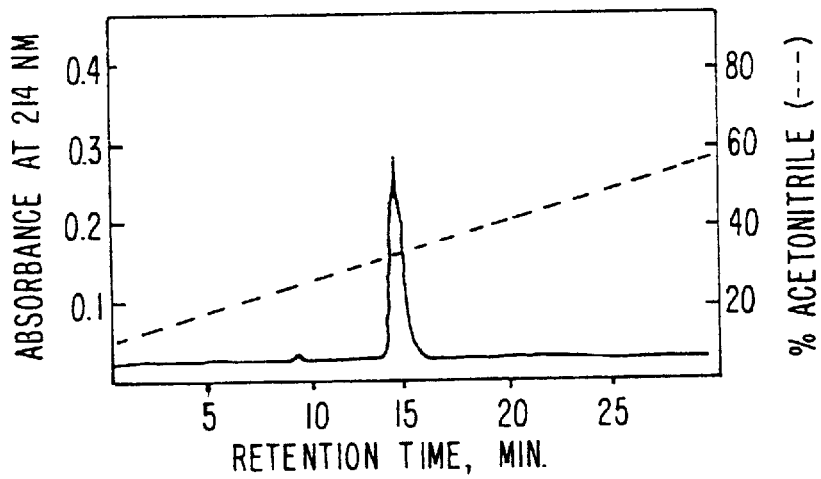
FIG. 7 shows a narrowbore HPLC analysis of acid-eluted peptides. 0.8 mg of purified complexes before and after $Ni^{2+}$•NTA chromatography were subjected to acetic acid extraction. The acid-eluted peptides were analyzed on a Waters (Millipore) HPLC system using narrowbore C-18 reverse phase column as described in the "Materials and General Protocols" section. (A) represents the retention time for 10 μg of [6×His-MBP(83-102)$Y^{83}$] peptide; (B) and (C) represent total peptides eluted from pre- and post-$Ni^{2+}$•NTA complexes.
Figure 7B:
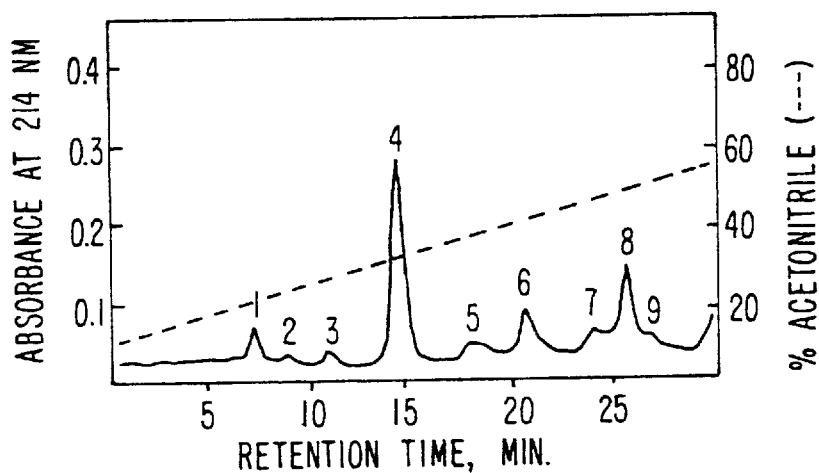
Figure 7C:
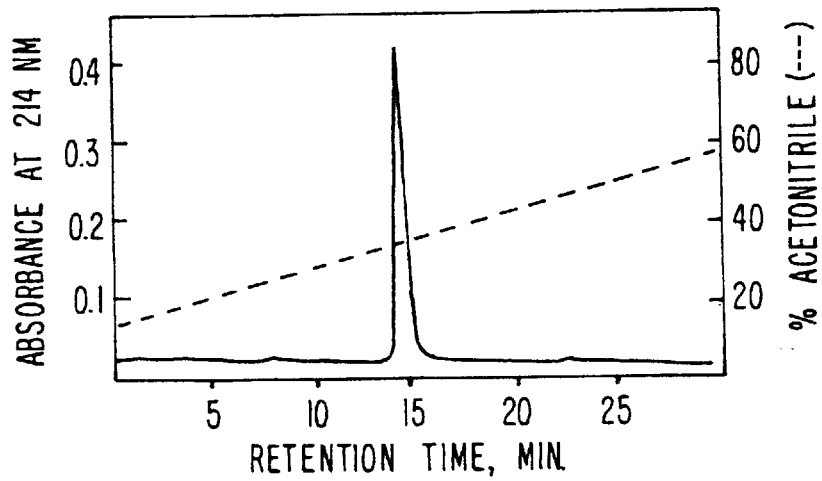

To demonstrate that the eluted complexes contain a single 6xHis-tagged MBP peptide, milligram quantities of complexes of HLA-DR2 with unlabeled [6xHis-MBP(83-102)$Y^{83}$] peptide were prepared. This was achieved by comparing the acid-eluted profile of bound peptides from pre- and post-Ni$^{2+}$•NTA complexes. The eluted peptides were characterized by narrowbore HPLC analysis (FIG. 7). Re-versephase HPLC analysis of 100% loaded complexes showed a single peak (FIG. 7C) with a retention time identical to that of pure [6×His-MBP(83-102)Y$^{83}$] peptide (FIG. 7A). In contrast, HPLC analysis of acid-eluted peptides from pre-Ni$^{2+}$•NTA complexes showed a significant amount of endogenous peptides along with the [6×His-MBP (83-102) Y$^{83}$] peptide. The identity of the peptide peak eluted from post Ni$^{2+}$•NTA complexes was confirmed by integrated microsequencing of first 18 amino acid residues from the N-terminal end.

Beside endogenously bound peptides, a significant portion of purified MHC class II molecules are often known to be associated with invariant chain polypeptides. The association of the invariant chain in the endoplasmic reticulum serves two important functions. First, it prevents class II molecules from binding peptides in the early stage of transport (Roche and Cresswell, *Nature,* 345:615 (1990); Roche and Cresswell, *Proc. Natl. Acad. Sci. USA,* 88:3150 (1991); Lotteau, et al., *Nature,* 348;600 (1990)). Second, it contains a cytoplasmic signal that targets the class II-invariant chain complexes to an acidic endosomal compartment (Bakke and Dobberstein, *Cell,* 63:707 (1990); Lotteau, et al., supra, 1990) where proteolysis and subsequent dissociation of the invariant chain takes place allowing antigenic peptides to bind prior to their expression at the cell surface. It has been shown that purified MHC II-invariant complexes are unable to bind antigenic peptides in vitro (Roche and Cresswell, supra, 1990; Newcomb and Creswell, *J. Immunol.,* 150:499 (1993)) and that both soluble and membrane associated invariant chains can block binding of peptides to MHC class II heterodimers (Lotteau, et al., supra, 1990; Roche, et al., *EMBO J.,* 11:2841 (1992)). To demonstrate the complete absence of invariant chain polypeptides in Ni$^{2+}$•NTA-eluted complexes of HLA-DR2 and [6×His-MBP(83-102)Y$^{83}$] peptide, two-dimensional gel electrophoresis was performed. In this gel system, IEF (pH 5-7/3-10) was carried out in the first dimension followed by 13.5% polyacrylamide-SDS in the second dimension. No invariant chains were detected in Ni$^{2+}$•NTA purified complexes. In contrast, purified HLA-DR2 showed multiple bands of invariant chain polypeptides with varying molecular sizes.

Figure 8:
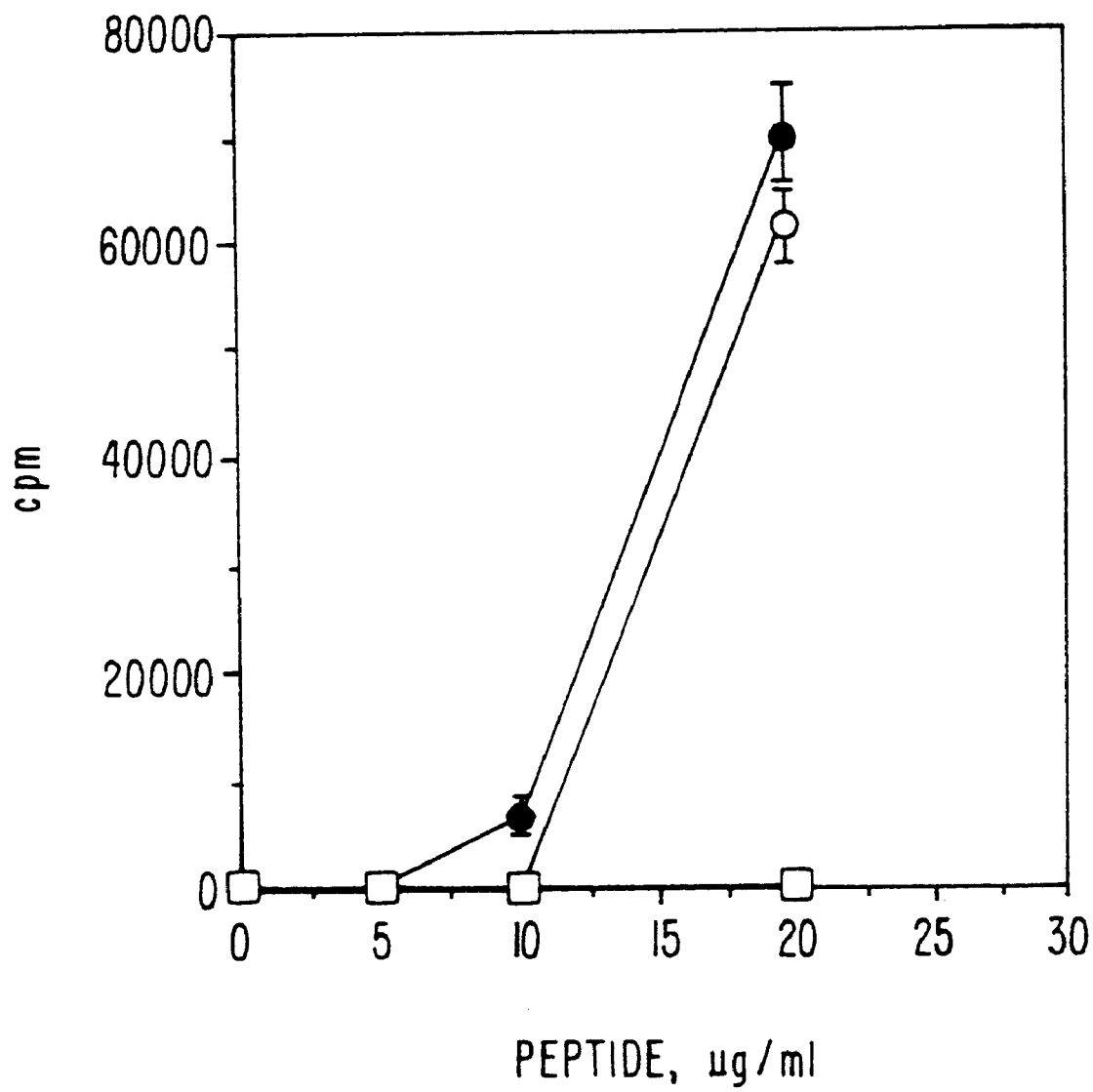
FIG. 8 shows proliferative response of T cells to MBP (84-102) and [6×His-MBP(83-102)$Y^{83}$] peptides. $2\times10^4$ cells were cultured in triplicate with $5\times10^5$ freshly irradiated autologous APCs in the presence of 0, 5, 10, 20 μg/ml of either [6xHis-MBP(83-102)Y$^{83}$] peptide. MBP(84-102) or with irrelevant peptide MBP(124-143). The degree of proliferation was measured by [$^3$H]thymidine incorporation. (●), response of DT cells in the presence of [6xHis-MBP (83-102)Y$^{83}$]; (○) in the presence of MBP(84-102) peptide; and (□) in the presence of irrelevant MBP(123-144) peptide.

Finally, to demonstrate that the presence of a 6×His tag in the antigenic epitope does not interfere with the functional ability of MHC II peptide complexes, in vitro proliferative response of a restricted T cell line (DT) was measured in the presence of autologous APCs and increasing concentrations of MBP(84-102) or [6×His-MBP(83-102)Y$^{83}$] peptide. As shown in FIG. 8, both MBP(84-102) and [6×His-MBP(83-102)Y$^{83}$] peptides were equally capable of stimulating T cells. The specificity of such T cell stimulation was shown by incubating DT cells in the presence of another peptide epitope MBP(124-143) from the same myelin basic protein under identical conditions.

These results together demonstrate the usefulness of metal chelate affinity chromatography for the purification of MHC-peptide complexes of defined composition. As previously mentioned, the 6×His-tag can be attached to either N- or C-terminus end of the peptide. In the examples using MBP(84-102) peptide, the tag was attached at the N terminus end because three proline residues towards the C-terminal end have been shown to be critical for binding. It will be readily apparent to those of ordinary skill in the art that the purified MHC-peptide complexes of the present invention having defined composition have significant applications. Recently, it has been demonstrated that the soluble MHC class II-peptide complexes can be used to prevent and treat various autoimmune diseases in animal models in an antigen-specific manner (Sharma, et al., *Proc. Nati. Acad. Sci. USA,* 88:11465 (1991); Bhayani, et al., unpublished results; Spack, et al., unpublished results). Preparation of homogeneous class II-peptide complexes of known composition may be an essential requirement for various human clinical applications. In addition, such complexes where a single peptide is bound to the MHC antigens will be useful in understanding the kinetics of MHC peptide interaction, crystallographic analysis, generating antibodies specific for a given complex, understanding allorecognition and finally to facilitate better understanding of the trimolecular complexes formed with a MHC antigen, a peptide and a T cell receptor.

The foregoing is offered primarily for purposes of illustration. It will be readily apparent to those skilled in the art that the operating conditions, materials, procedural steps and other parameters of the method described herein may be further modified or substituted in various ways without departing from the spirit and scope of the present invention.

What is claimed is:

1. A composition comprising an isolated MHC-peptide complex prepared by the following process:
   a) isolating an MHC component from a cell which produces said MHC component, said MHC component having an antigen binding site;
   b) contacting said MHC component with an antigenic peptide such that said peptide is associated with the antigen binding site of said MHC component thereby forming an MHC-peptide complex, wherein at least the first or the last amino acid of said antigenic peptide is a metal-chelating amino acid;
   c) contacting said MHC-peptide complex with a solid support having attached thereto a metal ion specific for the metal-chelating amino acid of said peptide, whereby said MHC-peptide complex is bound to said metal ion of said solid support; and
   d) eluting the bound MHC-peptide complex from said solid support.

2. A composition comprising a plurality of MHC-peptide complexes of defined composition, wherein at least the first or the last amino acid of the peptides of said MHC-peptide complexes is a metal-chelating amino acid.

3. A composition in accordance with claim 2 wherein said metal-chelating amino acid is histidine.

4. A composition in accordance with claim 3 wherein the peptide of said MHC-peptide complexes has incorporated therein six histidines.

5. A pharmaceutical composition comprising a pharmaceutically acceptable carrier and a plurality of MHC-peptide complexes of defined composition, wherein at least the first or the last amino acid of the peptides of said MHC-peptide complexes is a metal-chelating amino acid.

6. A composition in accordance with claim 5 wherein said metal-chelating amino acid is the last amino acid.

7. A composition in accordance with claim 5 wherein said metal-chelating amino acid is histidine.

8. A method of inducing anergy in a target T cell in a mammal, the method comprising administering to said mammal a therapeutically effective dose of a plurality of MHC-peptide complexes of defined composition, said MHC-peptide complexes consisting essentially of an isolated MHC component having an antigen binding site and an antigenic peptide, wherein at least the first or the last amino acid of said antigenic peptide is a metal-chelating amino acid and wherein said antigenic peptide is associated with the antigen binding site of said MHC component.

9. A method in accordance with claim 8 wherein said metal-chelating amino acid is the last amino acid.

10. A method in accordance with claim 8 wherein said metal-chelating amino acid is histidine.

11. A method in accordance with claim 8 wherein the target T cell is associated with an autoimmune disease selected from the group consisting of multiple sclerosis, rheumatoid arthritis and myasthenia gravis.

12. A method of treating autoimmune disease in a mammal, the method comprising administering to said mammal a therapeutically effective dose of a pharmaceutical composition, said pharmaceutical composition comprising a pharmaceutically acceptable carrier and a plurality of MHC-peptide complexes of defined composition, said MHC-peptide complexes consisting essentially of an isolated MHC component having an antigen binding site and an antigenic peptide, wherein at least the first or the last amino acid of said antigenic peptide is a metal-chelating amino acid, and wherein said antigenic peptide is associated with the antigen binding site of said MHC component.

13. A method in accordance with claim 12 wherein said metal-chelating amino acid is histidine.

14. A composition comprising an isolated MHC-peptide complex prepared by the following process:
   a) isolating an MHC component from a cell which produces said MHC component, said MHC component having an antigen binding site;
   b) contacting said MHC component with an antigenic peptide such that said peptide is associated with the antigen binding site of said MHC component thereby forming an MHC-peptide complex, wherein at least the first or the last amino acid of said antigenic peptide is a metal-chelating amino acid and wherein said antigenic peptide has from about two to about 10 metal-chelating amino acids incorporated therein at either the N- or C-terminus of said antigenic peptide;
   c) contacting said MHC-peptide complex with a solid support having attached thereto a metal ion specific for the metal-chelating amino acid of said peptide, whereby said MHC-peptide complex is bound to said metal ion of said solid support; and
   d) eluting the bound MHC-peptide complex from said solid support.

* * * * *